United States Patent
Sakurai et al.

(10) Patent No.: US 11,852,623 B2
(45) Date of Patent: Dec. 26, 2023

(54) MAGNETIC SENSOR FOR CAPTURING METAL WEAR PARTICLES IN SUSPENSION IN A LUBRICATION FLUID

(71) Applicant: NABTESCO CORPORATION, Tokyo (JP)

(72) Inventors: Kazuhiko Sakurai, Tokyo (JP); Takahito Azuma, Tokyo (JP); Atsushi Koike, Tokyo (JP)

(73) Assignee: NABTESCO CORPORATION, Tokyo (JP)

(*) Notice: Subject to any disclaimer, the term of this patent is extended or adjusted under 35 U.S.C. 154(b) by 130 days.

(21) Appl. No.: 17/100,054

(22) Filed: Nov. 20, 2020

(65) Prior Publication Data
US 2021/0181177 A1    Jun. 17, 2021

(30) Foreign Application Priority Data
Dec. 17, 2019 (JP) .................. 2019-227654

(51) Int. Cl.
*G01N 33/28* (2006.01)
*G01N 27/12* (2006.01)

(52) U.S. Cl.
CPC ....... *G01N 33/2858* (2013.01); *G01N 27/122* (2013.01)

(58) Field of Classification Search
CPC ............. G01N 33/2858; G01N 27/122; G01N 2015/0042; G01N 2015/0053; G01N 2015/0057; G01N 15/0606; G01N 15/06; G01N 15/0656; G01N 27/06; G01N 27/07; G01N 27/04; G01N 27/041; G01N 27/043
See application file for complete search history.

(56) References Cited

U.S. PATENT DOCUMENTS

| | | | | |
|---|---|---|---|---|
| 10,705,039 B2* | 7/2020 | Kiriyama | ........... | G01N 33/2858 |
| 11,499,931 B2* | 11/2022 | Sakurai | ............. | G01N 33/2858 |
| 2002/0145530 A1* | 10/2002 | Sato | .................. | G01N 33/2858 |
| | | | | 340/540 |

(Continued)

FOREIGN PATENT DOCUMENTS

| CN | 105548288 A | 5/2016 |
|---|---|---|
| DE | 102016220835 A1 | 4/2018 |

(Continued)

OTHER PUBLICATIONS

Extended European Search Report dated Aug. 27, 2021, issue in corresponding EP Application No. 20207763.2 with English translation (10 pgs.).

(Continued)

*Primary Examiner* — Kristina M Deherrera
*Assistant Examiner* — Fatemeh Esfandiari Nia
(74) *Attorney, Agent, or Firm* — Pillsbury Winthrop Shaw Pittman, LLP

(57) ABSTRACT

A sensor relating to one aspect of the present invention includes a first electrode, a second electrode arranged relative to the first electrode with a gap being provided therebetween, a sensor body having the first and second electrodes arranged therein, and a catching portion arranged in the gap and having an outer peripheral surface made of an insulating material. Electric connection is established along the outer peripheral surface via conductive particles gathering to the catching portion.

6 Claims, 21 Drawing Sheets

(56) References Cited

U.S. PATENT DOCUMENTS

| | | | |
|---|---|---|---|
| 2009/0314064 A1 | 12/2009 | Augros et al. | |
| 2014/0347032 A1 | 11/2014 | Reed et al. | |
| 2018/0031504 A1 | 2/2018 | Ricci et al. | |
| 2018/0223907 A1* | 8/2018 | Ito | F16C 33/667 |
| 2018/0275083 A1* | 9/2018 | Kiriyama | G01N 27/12 |
| 2019/0154608 A1 | 5/2019 | Nakamura et al. | |
| 2020/0088350 A1* | 3/2020 | Basso | B03C 1/286 |

FOREIGN PATENT DOCUMENTS

| | | |
|---|---|---|
| EP | 3279650 A1 | 2/2018 |
| JP | 2002-310967 A | 10/2002 |
| JP | 2005-331324 A | 12/2005 |
| JP | 2006-220542 A | 8/2006 |
| JP | 2006-300608 A | 11/2006 |
| JP | 2015-111060 A | 6/2015 |
| JP | 2017-190813 A | 10/2017 |
| JP | 2019-128311 A | 8/2019 |

OTHER PUBLICATIONS

Notice of Reasons for Rejection dated Jun. 6, 2023 issued in corresponding Japanese Patent Application No. 2019-227654 with English translation (12 pgs.).

Notice of Reasons for Rejection dated Aug. 15, 2023, issued in corresponding Japanese Patent Application No. 2019-227654 with English translation (9 pgs.).

\* cited by examiner

MAGNETIC SENSOR FOR CAPTURING METAL WEAR PARTICLES IN SUSPENSION IN A LUBRICATION FLUID

CROSS-REFERENCE TO RELATED APPLICATIONS

This application is based on and claims the benefit of priority from Japanese Patent Application Serial No. 2019-227654 (filed on Dec. 17, 2019), the contents of which are hereby incorporated by reference in their entirety.

TECHNICAL FIELD

The present invention relates to a sensor.

BACKGROUND

A mechanical device such as a speed reducer is housed in a housing filled with a lubricating oil in order to prevent the mechanical parts such as gears from being damaged. If the mechanical parts are worn out during operation of the mechanical device, abrasion powder (for example, a conductive substance such as iron powder) is mixed into the lubricating oil. The abrasion powder is, for example, of a conductive substance such as iron powder. As the mechanical parts are increasingly worn out and enter a wear-out failure period, which is defined in a failure rate curve (a bathtub curve), an increased amount of abrasion powder is mixed into the lubricating oil. For this reason, a sensor for sensing the amount of the abrasion powder in the lubricating oil allows for accurate preventive maintenance of the mechanical parts.

Such a sensor is known from and disclosed in, for example, Japanese Patent Application Publication No. 2005-331324 ("the '324 Publication"). The disclosed sensor includes a cup-shaped electrode arranged around the outer periphery of a permanent magnet and an electrode including a plurality of rod-shaped conductors arranged next to each other in the circumferential direction such that the rod-shaped conductors oppose the cup-shaped electrode. This sensor is configured to check how much the oil is contaminated by detecting the amount of the metal powder that can cause a short cut between the electrodes.

The present applicant has also filed a patent application for the sensor disclosed in Japanese Patent Application Publication No. 2019-128311 ("the '311 Publication").

The configurations disclosed in the '324 Publication, however, have the following disadvantages. Since the electrodes need to be arranged next to each other in the circumferential direction, the size reduction can not be accomplished beyond a certain level when the detectable amount of the metal powder is taken into consideration. Accordingly, the sensor disclosed in the '324 Publication is so large that it may not be accommodated within a small-volume oil pan. In recent years, in particular, there is a demand for smaller speed reducers and the like. This results in a demand for compact sensors suitable for smaller speed reducers and the like. At the same time, sensors are required to assure reliable operation and accurate failure prediction and detection. There is a demand for sensors satisfying all of these properties.

In addition, the sensor disclosed in the '311 Publication has a gap for detection formed between the electrodes in the radial direction. In order to prevent initial abrasion powder from causing the sensor to erroneously operate, the size of the gap can not be reduced. This creates a desire to realize a further smaller size.

SUMMARY

The present invention attempts to fulfill the objective of providing a sensor that can achieve a reduced size and high operational reliability.

An aspect of the present invention provides a sensor including a first electrode, a second electrode arranged relative to the first electrode with a gap being provided therebetween, a sensor body having the first and second electrodes arranged therein, and a catching portion arranged in the gap, where the catching portion has an outer peripheral surface made of an insulating material. Here, electric connection is established along the outer peripheral surface via conductive particles gathering to the catching portion. With such configurations, the above-mentioned objective is accomplished.

According to the sensor relating to one aspect of the present invention, the gap for detecting the conductive particles extends along the outer peripheral surface of the attracting portion. In this way, when compared with the case where the gap for detecting the conductive particles extends in the radial direction of the end surface of the sensor, the sensor can be reduced in size without compromising the detection sensitivity. In addition, since the direction of the detection can be configured to extend along the outer peripheral surface, the sensor can be reduced in size without compromising the detection sensitivity when compared with the case where a plurality of axially extending gaps for detection are arranged next to each other in the circumferential direction of the sensor.

A sensor relating to one aspect of the present invention includes a first electrode, a second electrode spaced away from the first electrode with a gap being provided therebetween in a circumferential direction, and an attracting portion arranged in the gap, where the attracting portion has an outer peripheral surface made of an insulating material. Here, the first electrode, the attracting portion and the second electrode are arranged next to each other in the circumferential direction, and conductive particles are attracted to the outer peripheral surface of the attracting portion, so that a short circuit is caused in the circumferential direction between the first electrode and the second electrode, resulting in a change in electrical resistance between the first electrode and the second electrode. With such configurations, the above-mentioned objective is accomplished.

According to the sensor relating to one aspect of the present invention, the gap for detecting the conductive particles extends along the outer peripheral surface of the attracting portion in the circumferential direction. In this way, when compared with the case where the gap for detecting the conductive particles extends in the radial direction of the end surface of the sensor, the sensor can be reduced in size without compromising the detection sensitivity. In addition, since the direction of the detection can be configured to extend in the circumferential direction along the outer peripheral surface of the attracting portion, the sensor can be reduced in size without compromising the detection sensitivity when compared with the case where a plurality of axially extending gaps for detection are arranged next to each other in the circumferential direction of the sensor.

The sensor relating to one aspect of the present invention may include a third electrode spaced away from the first and second electrodes with a gap being provided therebetween in the circumferential direction, and an attracting portion arranged in the gap, where the attracting portion has an outer peripheral surface made of an insulating material. Conductive particles may be attracted to the outer peripheral surface of the attracting portion, so that a short circuit is caused in the circumferential direction between the first electrode and the third electrode, resulting in a change in electrical resistance between the first electrode and the third electrode.

The sensor relating to one aspect of the present invention may include a fourth electrode spaced away from each of the first, second and third electrodes with a gap being provided therebetween in the circumferential direction, and an attracting portion arranged in the gap, where the attracting portion has an outer peripheral surface made of an insulating material. Here, conductive particles may be attracted to the outer peripheral surface of the attracting portion, so that a short circuit is caused in the circumferential direction between the first electrode and the fourth electrode, resulting in a change in electrical resistance between the first electrode and the fourth electrode.

In the sensor relating to one aspect of the present invention, outer peripheral surfaces of the first and second electrodes may form a side surface of a columnar body.

In the sensor relating to one aspect of the present invention, the first and second electrodes may be magnets and arranged such that magnetic flux lines extend radially outward from outer peripheral surfaces of the first and second electrodes.

A sensor relating to one aspect of the present invention includes a cylindrical sensor body, magnets in the sensor body, where the magnets divide the sensor body into four portions in a circumferential direction, and an attracting portion arranged such that the attracting portion fills gaps between the magnets in the sensor body. Here, the attracting portion protrudes radially outward beyond outer peripheral surfaces of the magnets, the magnets are magnetized in a radial direction, circumferentially adjacent ones of the magnets are magnetized oppositely, and the magnets serve as electrodes, and conductive particles are attracted to an outer peripheral surface of the attracting portion, so that a short circuit is caused in the circumferential direction between the magnets, resulting in a change in electrical resistance between the magnets serving as the electrodes. With such configurations, the above-mentioned objective is accomplished.

According to the sensor relating to one aspect of the present invention, the gaps for detecting the conductive particles extend along the outer peripheral surface of the attracting portion in the circumferential direction. In this way, when compared with the case where the gap for detecting the conductive particles extends in the radial direction of the end surface of the sensor, the sensor can be reduced in size without compromising the detection sensitivity. In addition, since the direction of the detection can be configured to extend in the circumferential direction along the outer peripheral surface of the attracting portion, the sensor can be reduced in size without compromising the detection sensitivity when compared with the case where a plurality of axially extending gaps for detection are arranged next to each other in the circumferential direction of the sensor.

A sensor relating to one aspect of the present invention includes a first electrode, a second electrode and a third electrode. Here, a first catching portion is arranged between the first electrode and the second electrode, a second catching portion is arranged between the second electrode and the third electrode, and the first, second and third electrodes are arranged next to each other in an axial direction of a sensor body. With such configurations, the above-mentioned objective is accomplished.

According to the sensor relating to one aspect of the present invention, the gaps for detecting the conductive particles extend along the outer peripheral surfaces of the catching portions and are arranged next to each other in the axial direction. In this way, when compared with the case where the gap for detecting the conductive particles extends in the radial direction of the end surface of the sensor, the sensor can be reduced in size without compromising the detection sensitivity. In addition, since the direction of the detection can be configured to extend in the axial direction along the outer peripheral surfaces of the attracting portions, the sensor can be reduced in size without compromising the detection sensitivity when compared with the case where a plurality of axially extending gaps for detection are arranged next to each other in the circumferential direction of the sensor.

A sensor relating to one aspect of the present invention includes a first electrode, a second electrode spaced away from the first electrode with a gap being provided therebetween in an axial direction, and an attracting portion arranged in the gap, where the attracting portion has an outer peripheral surface made of an insulating material. Here, the first electrode, the attracting portion and the second electrode are stacked on each other in the axial direction, and conductive particles are attracted to the outer peripheral surface of the attracting portion, so that a short circuit is caused in the axial direction between the first electrode and the second electrode, resulting in a change in electrical resistance between the first electrode and the second electrode. With such configurations, the above-mentioned objective is accomplished.

According to the sensor relating to one aspect of the present invention, the gap for detecting the conductive particles extends along the outer peripheral surface of the attracting portion in the axial direction. In this way, when compared with the case where the gap for detecting the conductive particles extends in the radial direction of the end surface of the sensor, the sensor can be reduced in size without compromising the detection sensitivity. In addition, since the direction of the detection can be configured to extend in the axial direction along the outer peripheral surface of the attracting portion, the sensor can be reduced in size without compromising the detection sensitivity when compared with the case where a plurality of axially extending gaps for detection are arranged next to each other in the circumferential direction of the sensor.

The sensor relating to one aspect of the present invention may include a third electrode spaced away from the first and second electrodes with a gap being provided therebetween in the axial direction, and an attracting portion arranged in the gap, where the attracting portion has an outer peripheral surface made of an insulating material. Here, the first, second and third electrodes and the attracting portions may be stacked on each other in the axial direction, and conductive particles may be attracted to the outer peripheral surface of the attracting portion, so that a short circuit is caused in the axial direction between the first electrode and the third electrode, resulting in a change in electrical resistance between the first electrode and the third electrode.

The sensor relating to one aspect of the present invention may include a fourth electrode spaced away from each of the first, second and third electrodes with a gap being provided therebetween in the axial direction, and an attracting portion arranged in the gap, where the attracting portion has an outer peripheral surface made of an insulating material. Here, the first to fourth electrodes and the attracting portions may be stacked on each other in the axial direction, and conductive particles may be attracted to the outer peripheral surface of the attracting portion, so that a short circuit is caused in the axial direction between the first electrode and the fourth electrode, resulting in a change in electrical resistance between the first electrode and the fourth electrode.

In the sensor relating to one aspect of the present invention, outer peripheral surfaces of the first and second electrodes may form a side surface of a columnar body.

In the sensor relating to one aspect of the present invention, the first and second electrodes may be magnets and arranged such that magnetic flux lines extend radially outward from outer peripheral surfaces.

A sensor relating to one aspect of the present invention includes a cylindrical sensor body, magnets in the sensor body, the magnets dividing the sensor body into three portions in an axial direction, and attracting portions arranged such that the attracting portions fill gaps in the axial direction between the magnets in the sensor body. Here, the magnets and the attracting portions are stacked on each other in the axial direction, the attracting portions protrude radially outward beyond outer peripheral surfaces of the magnets, the magnets are radially magnetized, axially adjacent ones of the magnets are oppositely magnetized, the magnets serve as electrodes, and conductive particles are attracted to outer peripheral surfaces of the attracting portions, so that a short circuit is caused in the axial direction between the magnets, resulting in a change in electrical resistance between the magnets serving as the electrodes. With such configurations, the above-mentioned objective is accomplished.

According to the sensor relating to one aspect of the present invention, the gaps for detecting the conductive particles extend along the outer peripheral surface of the attracting portion and arranged next to each other in the axial direction. In this way, when compared with the case where the gap for detecting the conductive particles extends in the radial direction of the end surface of the sensor, the sensor can be reduced in size without compromising the detection sensitivity. In addition, since the direction of the detection can be configured to extend in the axial direction along the outer peripheral surfaces of the attracting portions, the sensor can be reduced in size without compromising the detection sensitivity when compared with the case where a plurality of axially extending gaps for detection are arranged next to each other in the circumferential direction of the sensor.

A sensor relating to one aspect of the present invention includes a first electrode, a second electrode spaced away from the first electrode with a gap being provided therebetween in an axial direction, and a catching portion arranged in the gap, where the catching portion has an outer peripheral surface made of an insulating material. Here, the catching portion includes a plurality of catching portions having different axial lengths. With such configurations, the above-mentioned objective is accomplished.

According to the sensor relating to one aspect of the present invention, the first electrode, the attracting portion and the second electrode spaced away from each other in the axial direction and stacked on each other form a gap for detecting conductive particles, which extends along the outer peripheral surface of the attracting portion in the axial direction. In this way, when compared with the case where the gap for detecting the conductive particles extends in the radial direction of the end surface of the sensor, the sensor can be reduced in size without compromising the detection sensitivity. Furthermore, the attraction of the conductive particles is tuned by using a plurality of catching portions having different lengths in the axial direction. With this configuration, even when a large amount of conductive particles is attracted, the detection sensitivity of the sensor can be adjusted depending on the attraction of the conductive particles, so that the sensing can be reliably performed. In particular, when the sensor is placed in a large-size speed reducer or the like and a large amount of conductive particles is thus produced during the initial stage, the sensor can be configured such that the attraction of the conductive particles is limited or the sensing scheme is changed if a large amount of conductive particles is attracted. This enables the sensor to reliably perform the sensing.

A sensor relating to one aspect of the present invention includes a first electrode, a second electrode spaced away from the first electrode with a gap being provided therebetween in an axial direction, and an attracting portion arranged in the gap, where the attracting portion has an outer peripheral surface made of an insulating material. Here, the first electrode, the attracting portion and the second electrode are stacked on each other in the axial direction, and conductive particles are attracted to the outer peripheral surface of the attracting portion, so that a short circuit is caused in the axial direction between the first electrode and the second electrode, resulting in a change in electrical resistance between the first electrode and the second electrode. With such configurations, the above-mentioned objective is accomplished.

According to the sensor relating to one aspect of the present invention, the first electrode, the attracting portion and the second electrode spaced away from each other in the axial direction and stacked on each other form a gap for detecting conductive particles, which extends along the outer peripheral surface of the attracting portion in the axial direction. In this way, when compared with the case where the gap for detecting the conductive particles extends in the radial direction of the end surface of the sensor, the sensor can be reduced in size without compromising the detection sensitivity.

The sensor relating to one aspect of the present invention may include a third electrode spaced away from the first electrode with a gap being provided therebetween in the axial direction and spaced away from the second electrode with a gap being provided therebetween in the axial direction, and attracting portions arranged respectively in the gaps, where the attracting portions have an outer peripheral surface made of an insulating material. The first electrode, the attracting portion and the third electrode may be stacked on each other in the axial direction, and conductive particles may be attracted to the outer peripheral surface of the attracting portion, so that a short circuit is caused in the axial direction between the first electrode and the third electrode, resulting in a change in electrical resistance between the first electrode and the third electrode.

The sensor relating to one aspect of the present invention may include a fourth electrode spaced away from the first electrode with a gap being provided therebetween in the axial direction and spaced away from the second and third electrodes with a gap being provided therebetween in the axial direction, and attracting portions arranged in the gaps, where the attracting portions have an outer peripheral surface made of an insulating material. Conductive particles may be attracted to the outer peripheral surface of the attracting portion, so that a short circuit is caused in the axial direction between the first electrode and the fourth electrode, resulting in a change in electrical resistance between the first electrode and the fourth electrode.

In the sensor relating to one aspect of the present invention, the second, fourth and third electrodes may be spaced away from each other in the circumferential direction, and attracting portions may be arranged in gaps between the electrodes.

In the sensor relating to one aspect of the present invention, outer peripheral surfaces of the first and second electrodes may form a side surface of a columnar body.

In the sensor relating to one aspect of the present invention, a magnet may be positioned closer in the axial direction to the first electrode at least than to the second electrode, and the magnet may be arranged to form a magnetic flux line extending in the axial direction.

In the sensor relating to one aspect of the present invention, the first electrode may be a magnet.

A sensor relating to one aspect of the present invention includes a cylindrical sensor body. The sensor body includes a first electrode, an attracting portion and a second electrode stacked on each other in an axial direction, and a magnet magnetized in the axial direction. Conductive particles are attracted to an outer peripheral surface of the attracting portion, so that a short circuit is caused in the axial direction between the first electrode and the outer peripheral surface of the second electrode, resulting in a change in electrical resistance between the first electrode and the second electrode. With such configurations, the above-mentioned objective is accomplished.

According to the sensor relating to one aspect of the present invention, the first electrode, the attracting portion and the second electrode spaced away from each other in the axial direction and stacked on each other form a gap for detecting conductive particles, which extends along the outer peripheral surface of the attracting portion in the axial direction. In this way, when compared with the case where the gap for detecting the conductive particles extends in the radial direction of the end surface of the sensor, the sensor can be reduced in size without compromising the detection sensitivity.

In the sensor relating to one aspect of the present invention, the second electrode may be divided into portions in a circumferential direction of the sensor body.

Advantageous Effects

A sensor relating to one aspect of the present invention can produce the following effects. In the sensor body shaped like a columnar body, the gap for detection extending along the outer peripheral surface is positioned in an outermost manner. In this way, the sensing can be still performed accurately and the sensor can be reduced in size without compromising the sensitivity.

DESCRIPTION OF THE PREFERRED EMBODIMENTS

Figure 1:
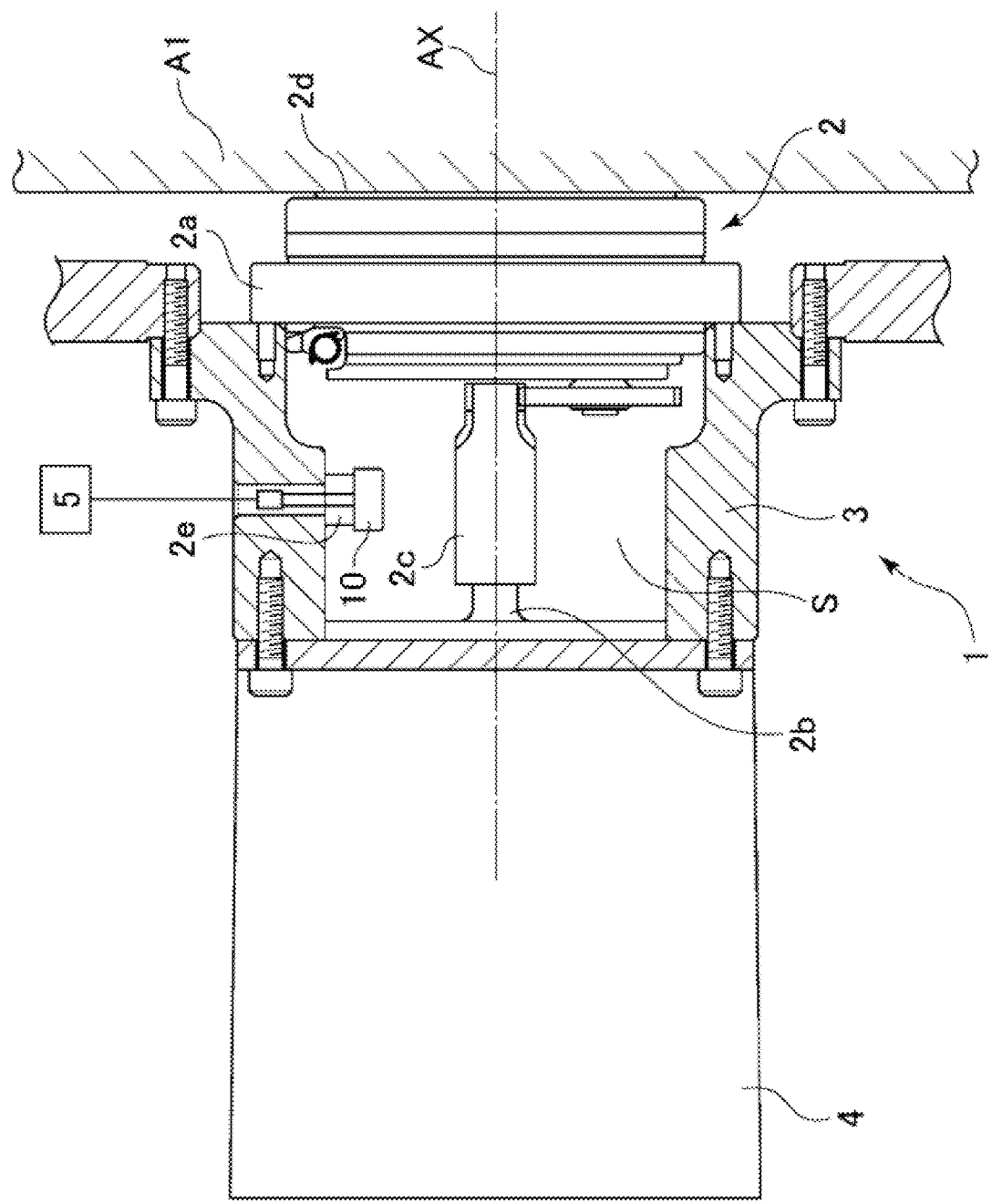
FIG. 1 is a sectional view showing one example of a mechanical device including a sensor relating to a first embodiment of the present invention.

The following describes a sensor relating to a first embodiment of the present invention with reference to the drawings. FIG. 1 is a sectional view showing one example of a mechanism including the sensor relating to the first embodiment of the present invention. In FIG. 1, the reference numeral 1 indicates the mechanism. The constituents common to more than one drawing are denoted by the same reference signs throughout the drawings. It should be noted that components in the drawings are not necessarily drawn to scale for the sake of convenience of description.

The mechanism 1 relating to the first embodiment is, for example, a mobile part such as a robot arm. The mechanism 1 includes a speed reducer 2, a flange 3 provided on the input side, a servomotor 4, and a device A1 provided on the output side, as shown in FIG. 1.

The speed reducer 2 includes a casing 2a mounted to the flange 3, an input shaft 2c connected to an output shaft 2b of the servomotor 4, and an output shaft 2d connected to the output-side device A1. The input shaft 2c and the output shaft 2d are supported such that it is capable of rotating about an axis AX relative to the casing 2a. The output from the servomotor 4 is input to the speed reducer 2 via the input shaft 2c, reduced in speed by the speed reducer 2, and then transmitted to the output-side device A1 via the output shaft 2d. Thus, the output-side device A1 and the flange 3 are capable of rotating relative to each other.

The flange 3 is a tubular member and houses therein at least a portion of the speed reducer 2. The servomotor 4 is mounted to the flange 3. An opening of the flange 3 at one end thereof in the direction along the axis AX is closed by the speed reducer 2, and an opening of the flange 3 at the other end thereof is closed by the servomotor 4. Thus, the flange 3 has a tightly closed hollow portion (a space S) formed therein. The space S contains therein a lubricating oil, so that the flange 3 also serves as an oil bath.

The casing 2a of the speed reducer 2 houses therein a gear mechanism, for example. The space within the casing 2a communicates with the space S within the flange 3. As the speed reducer 2 operates, the gear mechanism in the casing 2a rotates, which subsequently causes the lubricating oil to circulate between the space in the casing 2a and the space S in the flange 3. As the lubricating oil circulates, conductive particles mp (see FIG. 5) such as abrasion powder (conductive abrasion powder) produced in the speed reducer 2 moves into the space S in the flange 3.

In the space S, a sensor 10 is installed for sensing the amount of the conductive particles mp contained in the lubricating oil. The sensor 10 is fixed onto the flange 3 via, for example, a support member 2e. The sensor 10 uses magnets to gather the conductive particles (iron powder) mp, which are contained in the lubricating oil, between paired electrodes and uses a change in electrical resistance between the paired electrodes to sense the amount of the conductive particles mp in the lubricating oil. The sensor 10 may be alternatively positioned, for example, inside the casing 2a but can be at any position in the mechanism 1 as long as the position is within the space containing therein the lubricating oil.

Figure 2:
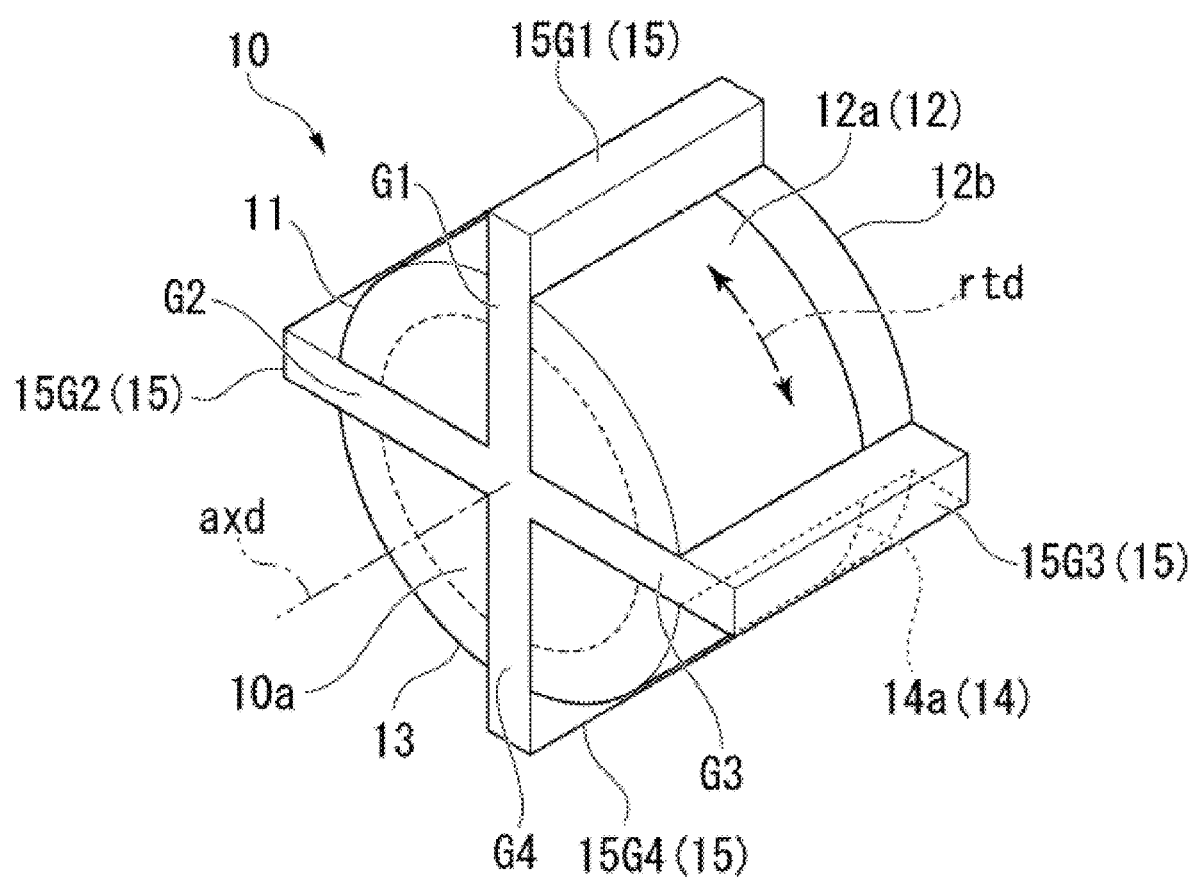
FIG. 2 is a perspective view showing the sensor relating to the first embodiment of the present invention.
Figure 3:
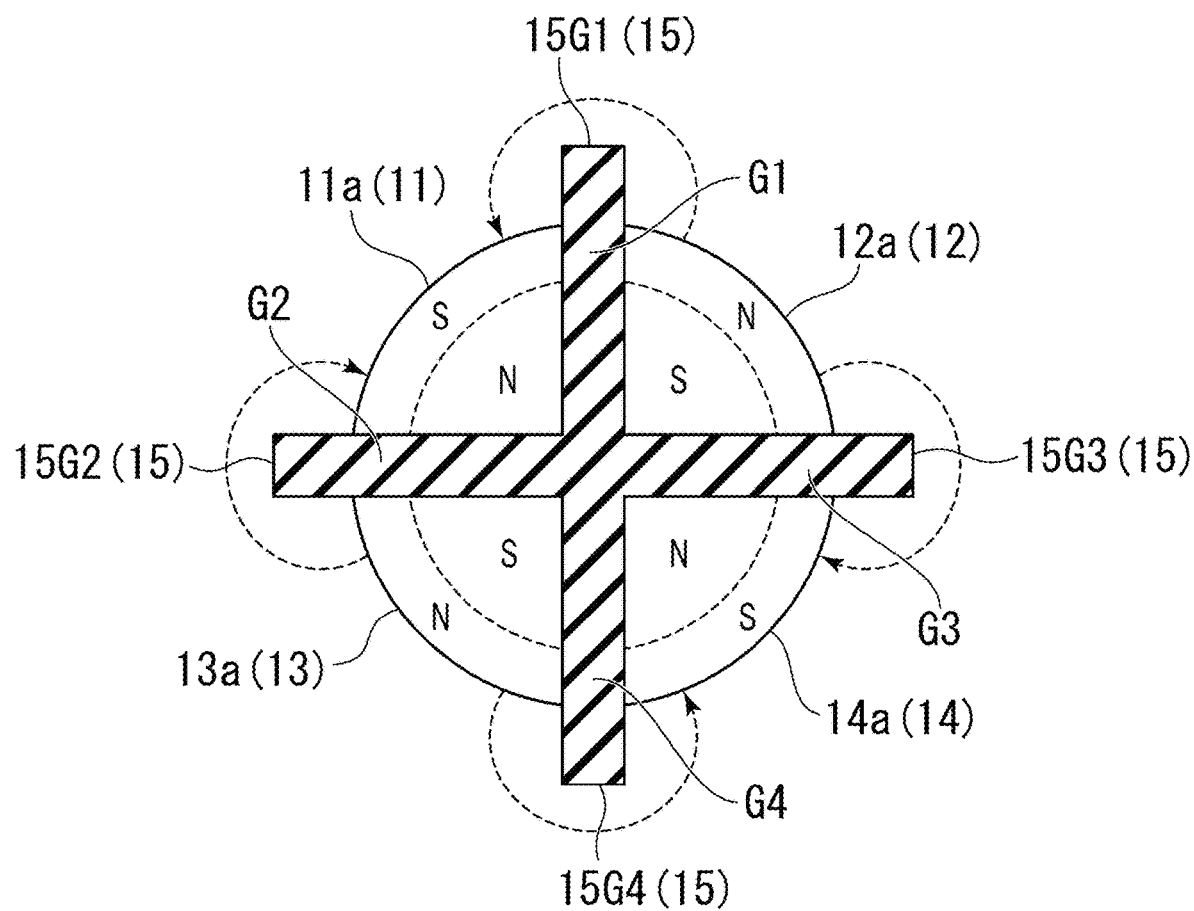
FIG. 3 is a sectional view showing the magnetic flux line direction in the sensor relating to the first embodiment of the present invention.
Figure 4:
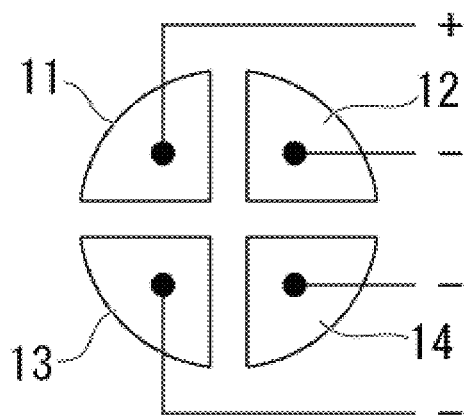
FIG. 4 shows how the electrodes are arranged in the sensor relating to the first embodiment of the present invention.

Next, with reference to FIGS. 2 to 4, a detailed description is given of the sensor relating to the present embodiment.

FIG. 2 is a perspective view showing the sensor relating to the present embodiment. FIG. 3 is an end view showing the sensor relating to the present embodiment. FIG. 4 shows how the electrodes are arranged in the sensor relating to the present embodiment. In FIG. 2, the reference numeral 10 denotes the sensor.

As shown in FIG. 2, the sensor 10 has a substantially cylindrical outer shape (shaped like a columnar body) around an axial line axd. The sensor 10 includes a first electrode 11, a second electrode 12, a third electrode 13, a fourth electrode 14 and an attracting portion (catching portion) 15.

An end surface 10a of the sensor 10 has a substantially circular shape extending in the direction orthogonal to the axial line axd. The first, second, third and fourth electrodes 11, 12, 13 and 14 each have a substantially fan-shaped sectional shape with a quadrant, when seen through the end surface 10a of the sensor 10. The first, second, third and fourth electrodes 11, 12, 13 and 14 all have substantially the same shape.

The first, second, third and fourth electrodes 11, 12, 13 and 14 are arranged such that they are rotated around the axial line axd. Accordingly, the first to fourth electrodes 11 to 14 are symmetrically arranged around the axial line axd. The electrodes 11 to 14 are arranged in the order of the first electrode 11, the second electrode 12, the fourth electrode 14, and the third electrode 13, clockwise in the circumferential direction rtd when seen through the end surface 10a.

The first, second, fourth and third electrodes 11, 12, 14 and 13 are all at the same position in the direction along the axial line axd. The first, second, fourth and third electrodes 11, 12, 14 and 13 are arranged such that their respective outer peripheral surfaces 11a to 14a form the same or flush cylindrical surface.

The first, second, third and fourth electrodes 11, 12, 13 and 14 all have the same length in the direction along the axial line axd. The first, second, third and fourth electrodes 11, 12, 13 and 14 are spaced away from each other in the direction extending in the end surface 10a. Gaps G1 to G4 are formed between the electrodes 11 to 14.

The gap G1 denotes the spacing distance in the circumferential direction rtd between the first electrode 11 and the second electrode 12. The gap G2 denotes the spacing distance in the circumferential direction rtd between the first electrode 11 and the third electrode 13. The gap G3 denotes the spacing distance in the circumferential direction rtd between the second electrode 12 and the fourth electrode 14. The gap G4 denotes the spacing distance in the circumferential direction rtd between the third electrode 13 and the fourth electrode 14.

The first, second, third and fourth electrodes 11, 12, 13 and 14 are all magnets. The magnets are, for example, permanent magnets. The first, second, third and fourth electrodes 11, 12, 13 and 14 are all magnetized in the radial direction of the sensor 10.

The first electrode 11 and the fourth electrode 14, which are symmetrically positioned with respect to the axial line axd, are magnetized such that their respective outer peripheral surfaces 11a and 14a are like poles. The second electrode 12 and the third electrode 13, which are symmetrically positioned with respect to the axial line axd, are magnetized such that their respective outer peripheral surfaces 12a and 13a are like poles. Here, the electrodes 11 to 14 are magnetized such that the adjacent ones of the electrodes 11 to 14 have different polarities.

For example, as shown in FIG. 3, the second electrode 12 and the third electrode 13 are magnetized such that their respective outer peripheral surfaces 12a and 13a are the N pole. The first electrode 11 and the fourth electrode 14 are magnetized such that their respective outer peripheral surfaces 11a and 14a are the S pole. The direction of magnetization can be reversed in all of the electrodes 11 to 14.

Arranged in the above described manner, the electrodes 11 to 14, which are formed by magnets, are attracted to each other by their magnetic force. As a result, the electrodes 11 to 14 can be secured onto the cross-shaped attracting portion 15 without the use of an adhesive portion such as an adhesive agent.

Between the electrodes 11 to 14, the attracting portion 15 is arranged. The attracting portion 15 is made of an insulating non-magnetic material, for example, resin. The attracting portion 15 has a section shaped like a cross when seen through the end surface 10a along the axial line axd.

The attracting portion 15 has an attracting protrusion 15G1 filling the gap G1 between the first electrode 11 and the second electrode 12 and protruding radially outward beyond the outer peripheral surfaces 11a, 12a. The attracting portion 15 has an attracting protrusion 15G2 filling the gap G2 between the first electrode 11 and the third electrode 13 and protruding radially outward beyond the outer peripheral surfaces 11a, 13a.

The attracting portion 15 has an attracting protrusion 15G3 filling the gap G3 between the second electrode 12 and the fourth electrode 14 and protruding radially outward beyond the outer peripheral surfaces 12a, 14a. The attracting portion 15 has an attracting protrusion 15G4 filling the gap G4 between the third electrode 13 and the fourth electrode 14 and protruding radially outward beyond the outer peripheral surfaces 13a, 14a.

The attracting protrusions 15G1 to 15G4 are formed such that they all have the same protruding height in the radial direction. Alternatively, the attracting protrusions 15G1 to 15G4 may be formed such that they have any, for example, different protruding heights in the radial direction. By adjusting the protruding heights of the attracting protrusions 15G1 to 15G4 in the radial direction, the sensitivity of the detection, described below, can be tuned.

The size, in the circumferential direction rtd, of the gaps G1 to G4 between the electrodes 11 to 14 is larger than the size of the conductive substance that can be contained in the lubricating oil. For example, the conductive substance has a size of approximately 1.0 μm to 100 μm. The gaps G1 to G4 are preferably arranged at such intervals that no short circuit is created by the iron powder resulting from initial wear period. The gaps G1 to G4 all have the same size in the circumferential direction rtd.

Between the electrodes 11 to 14, which are magnets, magnetic flux lines run radially outside the attracting protrusions 15G1 to 15G4 to connect together the electrodes 11 to 14, as shown in FIG. 3. Between the first electrode 11 and the second electrode 12, magnetic flux lines start from the outer peripheral surface 12a of the second electrode 12, which is the N pole, run radially outside the attracting protrusion 15G1, and proceed toward the outer peripheral surface 11a of the first electrode 11, which is the S pole. Between the first electrode 11 and the third electrode 13, magnetic flux lines start from the outer peripheral surface 13a of the third electrode 13, which is the N pole, run radially outside the attracting protrusion 15G2, and proceed toward the outer peripheral surface 11a of the first electrode 11, which is the S pole.

Between the fourth electrode 14 and the second electrode 12, magnetic flux lines start from the outer peripheral surface 12a of the second electrode 12, which is the N pole, run radially outside the attracting protrusion 15G3, and proceed toward the outer peripheral surface 14a of the fourth electrode 14, which is the S pole. Between the fourth electrode 14 and the third electrode 13, magnetic flux lines start from the outer peripheral surface 13a of the third electrode 13, which is the N pole, run radially outside the attracting protrusion 15G4, and proceed toward the outer peripheral surface 14a of the fourth electrode 14, which is the S pole.

The electrodes 11 to 14 can have a non-magnetic conductor portion at an end thereof opposite the end surface 10a. If such is the case, in the electrodes 11 to 14, the magnet and the conductor portion are in contact with each other so that the electrodes 11 to 14 are electrically conductive. FIG. 2 shows the conductor portion 12b of the second electrode 12.

Output lines are connected to the first, second, third and fourth electrodes 11, 12, 13 and 14. The first, second, third and fourth electrodes 11, 12, 13 and 14 are respectively electrically connected to a sensing unit 5 (see FIG. 1) via the output lines. The electrodes 11 to 14 are insulated from each other. As shown in FIG. 4, the first electrode 11 and one of the other electrodes 12 to 14 form a pair of electrodes, and the attracting portion 15 arranged between the paired electrodes constitutes a single detecting unit together with the pair of electrodes. In FIG. 4, the electrode pairs constituting the detecting units are denoted by assigning the sign "+" to the output line of the first electrode 11 and "−" to the output lines of the other electrodes 12 to 14.

Figure 5:
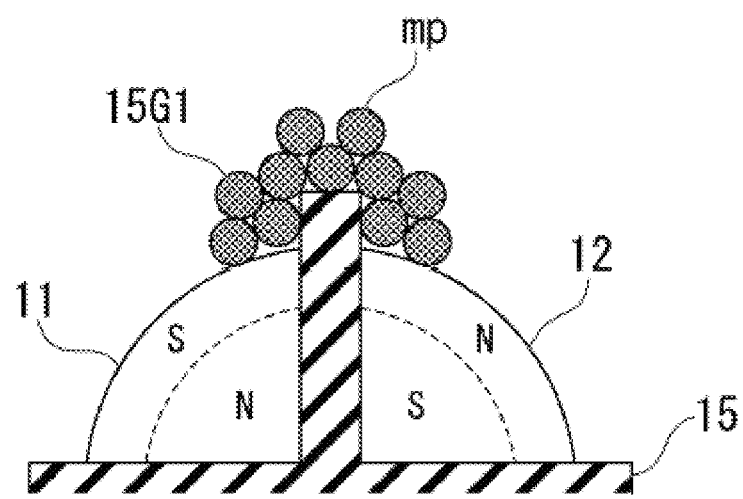
FIG. 5 is a sectional view showing how detection is performed in the sensor relating to the first embodiment of the present invention.

FIG. 5 is a sectional view showing how detection is performed in the sensor relating to the present embodiment. In the present embodiment, the sensor 10 includes three detecting units, corresponding to the second, third and fourth electrodes 12, 13 and 14. There are no particular limitations on the number of the electrodes 12 to 14 and the number of the detecting units. Since the electrodes 11 to 14 of the sensor 10, which are magnets, produce magnetic flux lines between the paired ones of the electrodes 11 to 14, the conductive particles (abrasion powder) mp contained in the lubricating oil are attracted to the attracting portion 15, as shown in FIG. 5. Since the magnetic flux lines formed by the electrodes 11 to 14 start from the position immediately close to the attracting portion 15 and run radially, the conductive particles mp can be attracted highly efficiently. If the conductive particles mp are gathered in the vicinity of the attracting portion 15 in this manner, the detecting units experience a change in electrical resistance. While no conductive particles (abrasion powder) mp are attracted, the detecting units may exhibit the same electrical resistance.

In the present embodiment, the detecting units corresponding to the second and third electrodes 12 and 13 are connected to each other in parallel. Between the first electrode 11 and the second electrode 12, voltage is applied by the same voltage source. Between the first electrode 11 and the third electrode 13, voltage is applied by the same voltage source. If the conductive particles mp are gathered in the vicinity of the attracting protrusion 15G1, the detecting unit corresponding to the second electrode 12 experiences a change in electrical resistance. If the conductive particles mp are gathered in the vicinity of the attracting protrusion 15G2, the detecting unit corresponding to the third electrode 13 experiences a change in electrical resistance.

The sensing unit 5 is configured to sense a change in electrical resistance between the first electrode 11 and the second electrode 12. The sensing unit 5 includes a sensor drive circuit for predicting a failure of the parts constituting the mechanism 1 based on, for example, a change in electrical resistance caused by the gathering of the conductive particles mp in the vicinity of the attracting protrusion 15G1. If the conductive particles mp contained in the lubricating oil are gathered in the vicinity of the attracting protrusion 15G1, this causes a drop in electrical resistance (or a short circuit) between the first electrode 11 and the second electrode 12 to which voltage is being applied, resulting in a change in output level of the output lines. The sensing unit 5 senses such a change in electrical resistance, thereby predicting a failure of the parts constituting the mechanism 1.

Likewise, the sensing unit 5 is configured to sense a change in electrical resistance between the first electrode 11 and the third electrode 13. The sensing unit 5 includes a sensor drive circuit for predicting a failure of the parts constituting the mechanism 1 based on, for example, a change in electrical resistance caused by the gathering of the conductive particles mp in the vicinity of the attracting protrusion 15G2. If the conductive particles mp contained in the lubricating oil are gathered in the vicinity of the attracting protrusion 15G3, this causes a drop in electrical resistance (or a short circuit) between the first electrode 11 and the third electrode 13 to which voltage is being applied, resulting in a change in output level of the output lines. The sensing unit 5 senses such a change in electrical resistance, thereby predicting a failure of the parts constituting the mechanism 1.

Between the first electrode 11 and the fourth electrode 14, voltage is applied by the same voltage source. If the conductive particles mp are gathered in the vicinity of both of the attracting protrusions 15G1 and 15G3, the detecting unit corresponding to the fourth electrode 14 experiences a change in electrical resistance. Alternatively, if the conductive substance is gathered in the vicinity of both of the attracting protrusions 15G2 and 15G4, the detecting unit corresponding to the fourth electrode 14 experiences a change in electrical resistance.

The sensing unit 5 is configured to sense a change in electrical resistance between the first electrode 11 and the fourth electrode 14. The sensing unit 5 includes a sensor drive circuit for predicting a failure of the parts constituting the mechanism 1 based on, for example, a change in electrical resistance caused by the gathering of the conductive particles mp in the vicinity of the attracting protrusions 15G1 and 15G3. If the conductive particles mp contained in the lubricating oil are gathered in the vicinity of both of the attracting protrusions 15G1 and 15G3, this causes a drop in electrical resistance (or a short circuit) between the first electrode 11 and the fourth electrode 14 to which voltage is being applied, resulting in a change in output level of the output lines. The sensing unit 5 senses such a change in electrical resistance, thereby predicting a failure of the parts constituting the mechanism 1. This prediction is not made possible until the conductive particles mp are gathered in the vicinity of both of the attracting protrusions 15G1 and 15G3.

Likewise, the sensing unit 5 includes a sensor drive circuit for predicting a failure of the parts constituting the mechanism 1 based on, for example, a change in electrical resistance caused by the gathering of the conductive particles mp in the vicinity of the attracting protrusions 15G2 and 15G4. If the conductive particles mp contained in the lubricating oil are gathered in the vicinity of both of the attracting protrusions 15G2 and 15G4, this causes a drop in electrical resistance (or a short circuit) between the first electrode 11 and the fourth electrode 14 to which voltage is being applied, resulting in a change in output level of the output lines. The sensing unit 5 senses such a change in electrical resistance, thereby predicting a failure of the parts constituting the mechanism 1. This prediction is not made possible until the conductive particles mp are gathered in the vicinity of both of the attracting protrusions 15G2 and 15G4.

As described above, the change in electrical resistance experienced by the detecting unit corresponding to the second electrode 12 and the detecting unit corresponding to the third electrode 13 is used to detect a change in electrical resistance in one attracting protrusion, which is selected from the attracting protrusions 15G1 and 15G2. On the other hand, the change in electrical resistance experienced by the detecting unit corresponding to the fourth electrode 14 is used to detect a change in electrical resistance in two attracting protrusions, which are either the attracting protrusions 15G1 and 15G3, or the attracting protrusions 15G2 and 15G4. This means that the plurality of detecting units are capable of sensing different conditions. In other words, the detecting units are configured to detect a change in electrical resistance in two stages. The detecting units can perform the sensing in two stages and two systems. Accordingly, the reliability of the failure prediction can be improved.

The sensing unit 5 outputs a signal when a designated one of the detecting units experiences a change in electrical resistance. For example, the sensing unit 5 may be configured to output a signal to a higher-level control device such as a manipulator when two or more of the detecting units experience a drop in electrical resistance, or configured to output a signal when all of the detecting units experience a drop in electrical resistance.

The drop in electrical resistance may be indicated by an ON signal and an OFF signal corresponding to electrical disconnection and connection. The sensing unit 5 may sense two states of electrical disconnection and connection (hereinafter, may be referred to as "perform digital sensing"). The sensing unit 5 may be connected to a higher-level control device (not shown) such as a manipulator in a wired or wireless manner. The higher-level control device may be configured to, upon reception of a signal from the sensing unit 5, issue an alert for demanding maintenance of, for example, the speed reducer 2 with a predetermined notifying device (for example, a display or voice output device).

As described above, the sensor 10 of the present embodiment includes the plurality of detecting units, and the sensing unit 5 outputs a signal when designated one or more of the detecting units experience a drop in electrical resistance. In this way, the sensing unit 5 can be configured to output no signal when just one of the detecting units experiences a change in electrical resistance caused by initial abrasion powder but the other detecting units do not experience a change in electrical resistance. Accordingly, the sensor can be prevented from operating unexpectedly. Furthermore, in the sensor 10, the sensing unit 5 can be configured to output a signal under a designated condition. Therefore, the single sensor 10 can be configured to output a signal in a timely and optimal manner for individual users, who have different requests for failure prediction timing.

While no conductive particles mp are attracted, the detecting units can exhibit the same electrical resistance. This can lower the voltage to be applied to the sensor 10. The detecting units are connected in parallel to each other. This can lower the voltage applied between the paired electrodes in each detecting unit. The sensor 10 is preferably positioned such that the first electrode 11, which forms the detecting unit with every one of the other electrodes 12 to 14, deals with a large amount of conductive particles mp.

According to the sensor 10 relating to the present embodiment, the gaps G1 to G4 for detecting the conductive particles mp are arranged next to each other in the circumferential direction rtd along the outer peripheral surfaces 11a to 14a. In this way, when compared with the case where such gaps for detecting conductive particles are arranged next to each other in the radial direction on the end surface 10a of the sensor 10, the sensor 10 can be reduced in size without compromising the detection sensitivity. In addition, the direction of the detection performed by the detecting units can be configured to extend in the circumferential direction rtd along the outer peripheral surfaces 11a to 14a. Accordingly, when compared with the case where a plurality of detection gaps extending in the axial line axd direction are arranged next to each other in the circumferential direction of the sensor, the sensor 10 can be reduced in size without compromising the detection sensitivity. Furthermore, since the magnetic flux lines produced by the electrodes 11 to 14, which are magnets, start from the position immediately close to the attracting portion 15 and run radially, the conductive particles mp can be attracted highly efficiently. Thus, the size reduction can not result in lower attraction efficiency. Furthermore, the sensor 10 of the present embodiment can be constituted by a reduced number of parts, assembled easily and manufactured at a reduced cost.

Figure 6A:
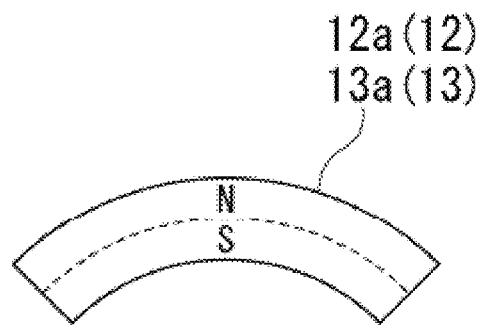
FIGS. 6A and 6B show another example of the magnets included in the sensor relating to the first embodiment of the present invention.
Figure 6B:
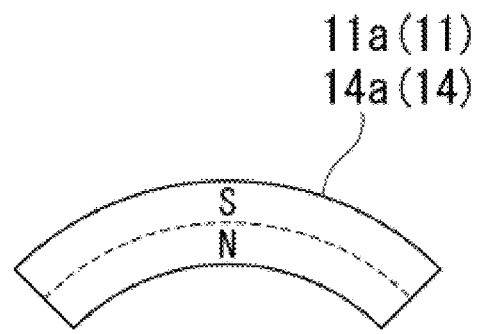

FIGS. 6A and 6B show another example of the magnets included in the sensor relating to the present embodiment. In the sensor 10 relating to the present embodiment, the magnets forming the electrodes 11 to 14 have a section shaped like a fan. As shown in FIGS. 6A and 6B, however, the magnets forming the electrodes 11 to 14 can have a section shaped like a circumferential quarter of a ring. In this case, all of the electrodes 11 to 14 also have a direction of magnetization extending in the radial direction of the sensor 10. The second electrode 12 and the third electrode 13 are magnetized such that their respective outer peripheral surfaces 12a and 13a are like poles. The first electrode 11 and the fourth electrode 14 are magnetized such that their respective outer peripheral surfaces 11a and 14a are like poles. Here, the electrodes 11 to 14 are magnetized such that the adjacent ones of the electrodes 11 to 14 are different poles.

Arranged in the above-described manner, the electrodes 11 to 14, which are formed by magnets, are attracted to each other by their magnetic force. As a result, the electrodes 11 to 14 can be secured onto the cross-shaped attracting portion 15 without the use of an adhesive portion such as an adhesive agent.

Figure 7:
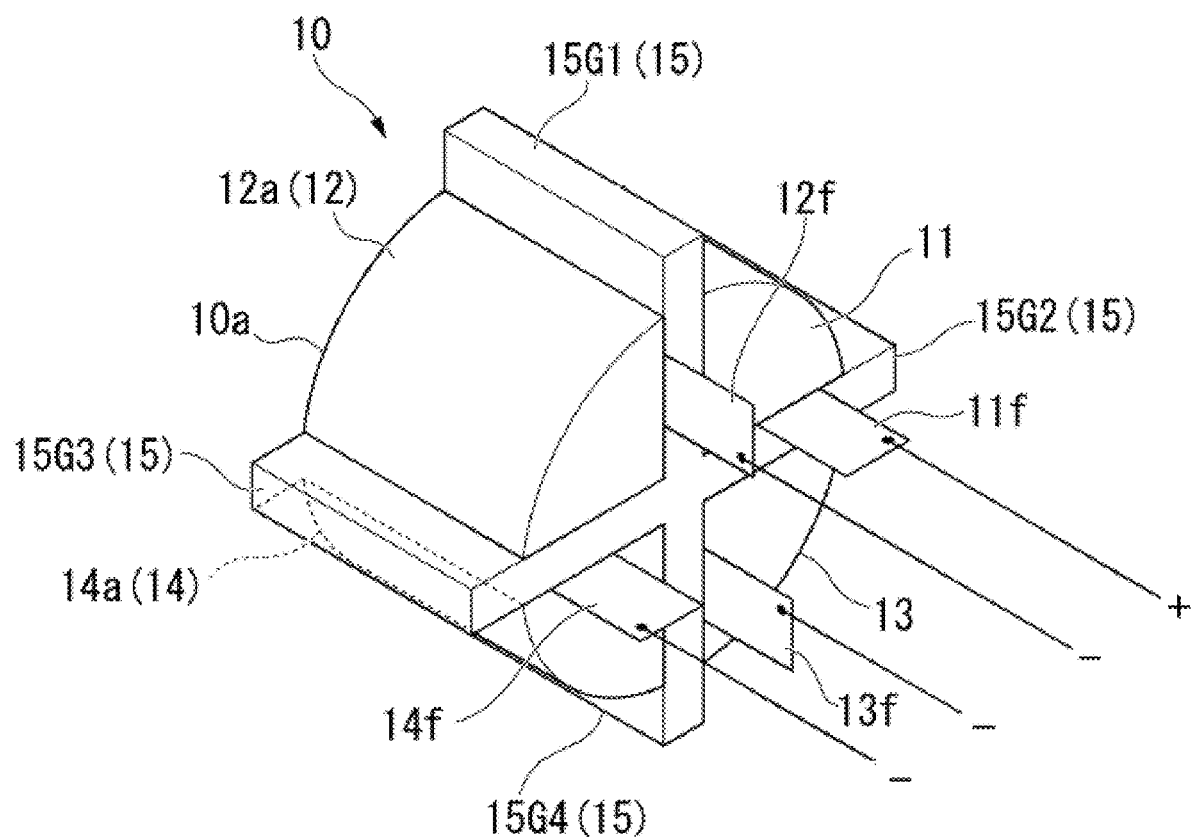
FIG. 7 is a perspective view showing another example of the sensor relating to the first embodiment of the present invention.

FIG. 7 is a perspective view showing another example of the sensor relating to the present embodiment. In the sensor 10 relating to the present embodiment, the output lines extending from the electrodes 11 to 14 can be formed by using flexible substrates 11f to 14f, as shown in FIG. 7.

The output line connected to the first electrode 11 is formed by the flexible substrate 11f, which is interposed between the first electrode 11 and the attracting portion 15. A portion of the flexible substrate 11f that is in contact with the first electrode 11 is electrically conductive as, for example, coating has been removed and thus in electrical communication with the first electrode 11. In addition, since the electrodes 11 to 14, which are formed by magnets, are attracted to each other due to their magnetic force, the flexible substrate 11f is secured while being sandwiched between the first electrode 11 and the attracting portion 15.

As a result, the flexible substrate 11f can be fixedly connected to the first electrode 11 without the use of an adhesive agent or the like and with the electrical connection being maintained. In the same manner, in the sensor 10 relating to the present embodiment, the flexible substrate 12f is fixedly connected to the second electrode 12, the flexible substrate 13f is fixedly connected to the third electrode 13, and the flexible substrate 14f is fixedly connected to the fourth electrode 14.

FIG. 7 shows that the flexible substrate 11f is interposed between the first electrode 11 and the attracting protrusion 15G2, but the flexible substrate 11f can be alternatively interposed between the first electrode 11 and the attracting protrusion 15 G1.

Figure 8:
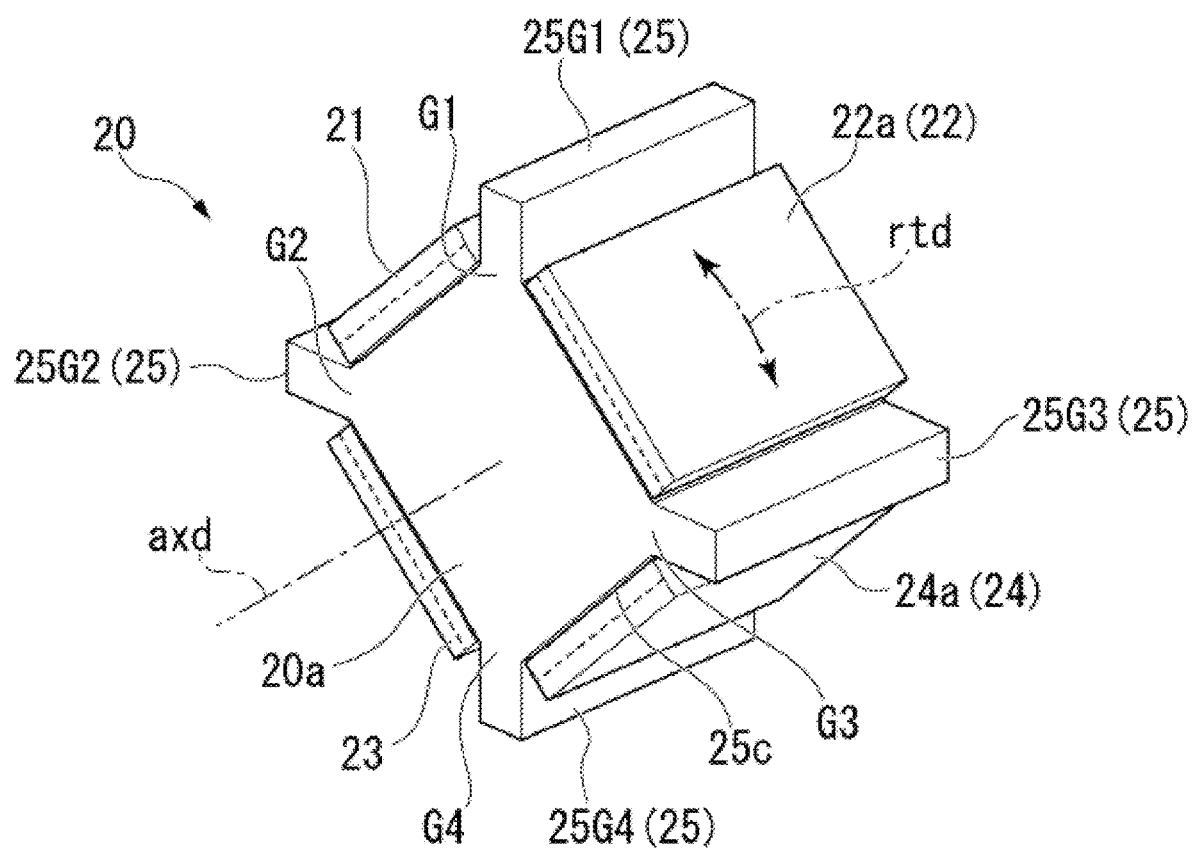
FIG. 8 is a perspective view showing a sensor relating to a second embodiment of the present invention.
Figure 9:
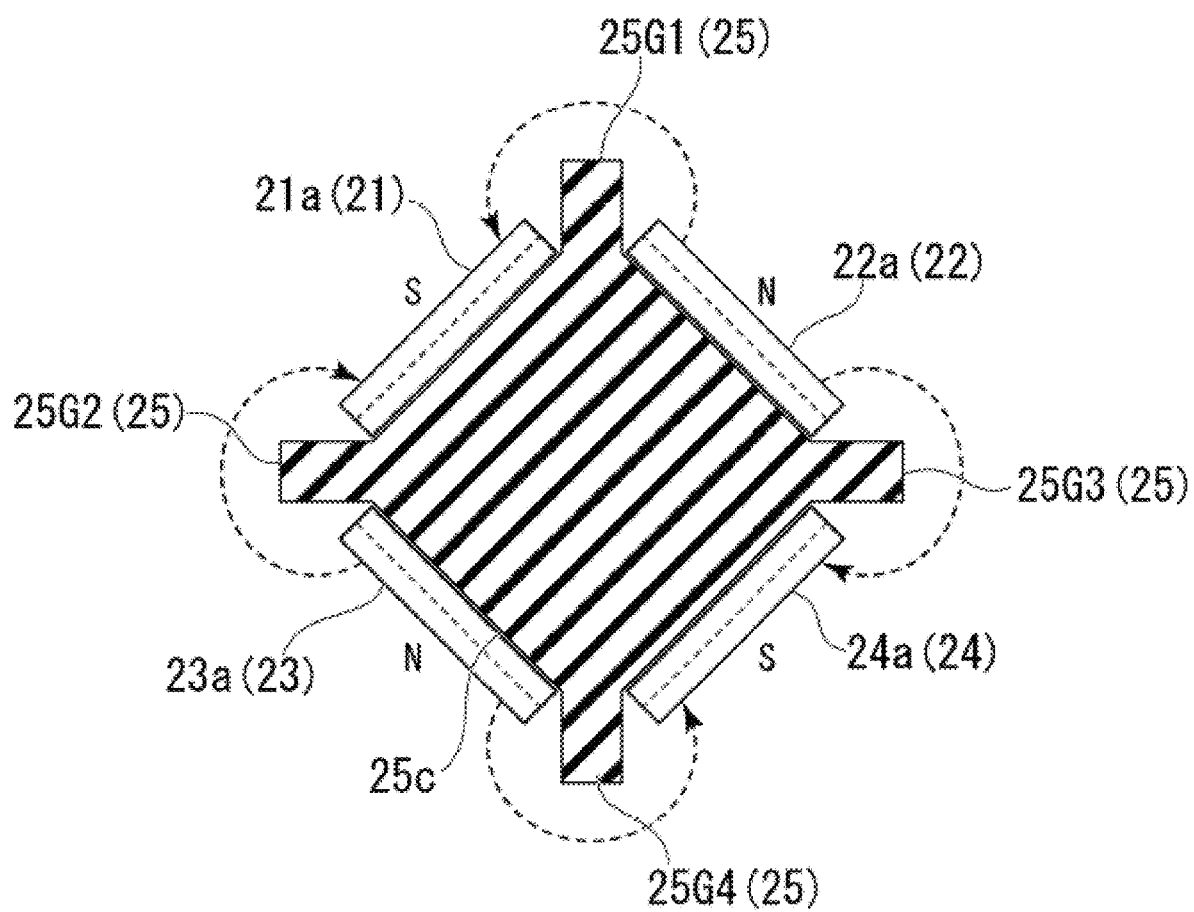
FIG. 9 is a sectional view showing the magnetic flux line direction in the sensor relating to the second embodiment of the present invention.

The following describes a sensor relating to a second embodiment of the present invention with reference to the drawings. FIG. 8 is a perspective view showing the sensor relating to the present embodiment. FIG. 9 is an end view showing the sensor relating to the present embodiment. In FIG. 8, the reference numeral 20 denotes the sensor. The second embodiment is different from the above-described first embodiment in terms of the outer shape of the sensor and magnets. The constituents of the mechanism 1 illustrated in FIG. 1 are not described here.

As shown in FIG. 8, the sensor 20 has a substantially prismatic outer shape (shaped like a column) around an axial line axd. The sensor 20 includes a first electrode 21, a second electrode 22, a third electrode 23, a fourth electrode 24 and an attracting portion (catching portion) 25.

An end surface 20a of the sensor 20 has a substantially rectangular shape extending in the direction orthogonal to the axial line axd. The first, second, third and fourth electrodes 21, 22, 23 and 24 form side surfaces of a prism. The first, second, third and fourth electrodes 21, 22, 23 and 24 have a section substantially shaped like a rectangle, when seen through the end surface 20a of the sensor 20. The electrodes 21 to 24 are shaped like a rectangular flat plate. The first, second, third and fourth electrodes 21, 22, 23 and 24 all have substantially the same shape.

The first, second, third and fourth electrodes 21, 22, 23 and 24 are arranged such that they are rotated around the axial line axd. Accordingly, the first to fourth electrodes 21 to 24 are symmetrically arranged around the axial line axd. The electrodes 21 to 24 are arranged in the order of the first electrode 21, the second electrode 22, the fourth electrode 24, and the third electrode 23, clockwise in the circumferential direction rtd when seen through the end surface 20a.

The first, second, fourth and third electrodes 21, 22, 24 and 23 are all at the same position in the direction along the axial line axd. The first, second, fourth and third electrodes 21, 22, 24 and 23 are arranged such that their respective outer peripheral surfaces 21a to 24a are at the same distance from the axial line axd and form the sides of square section.

The first, second, third and fourth electrodes 21, 22, 23 and 24 all have the same length in the direction along the axial line axd. The first, second, third and fourth electrodes 21, 22, 23 and 24 are spaced away from each other in the direction extending in the end surface 20a. Gaps G1 to G4 are formed between the electrodes 21 to 24.

The gap G1 denotes the spacing distance in the circumferential direction rtd between the first electrode 21 and the second electrode 22. The gap G2 denotes the spacing distance in the circumferential direction rtd between the first electrode 21 and the third electrode 23. The gap G3 denotes the spacing distance in the circumferential direction rtd between the second electrode 22 and the fourth electrode 24. The gap G4 denotes the spacing distance in the circumferential direction rtd between the third electrode 23 and the fourth electrode 24.

The first, second, third and fourth electrodes 21, 22, 23 and 24 are all magnets. The magnets are, for example, permanent magnets. In all of the first, second, third and fourth electrodes 21, 22, 23 and 24, the direction of magnetization extends in the radial direction of the sensor 20. In other words, the electrodes 21 to 24 are thin plate-shaped magnets magnetized such that the front surface, which is the principal surface of the plate, and the back surface are different poles.

The first electrode 21 and the fourth electrode 24, which are symmetrically positioned with respect to the axial line axd and oppose each other, are magnetized such that their respective outer peripheral surfaces 21a and 24a are like poles. The second electrode 22 and the third electrode 23, which are symmetrically positioned with respect to the axial line axd and oppose each other, are magnetized such that their respective outer peripheral surfaces 22a and 23a are like poles. Here, the electrodes 21 to 24 are magnetized such that the adjacent ones of the electrodes 21 to 24 are different poles.

For example, as shown in FIG. 9, the second electrode 22 and the third electrode 23 are magnetized such that their respective outer peripheral surfaces 22a and 23a are N poles. The first electrode 21 and the fourth electrode 24 are magnetized such that their respective outer peripheral surfaces 21a and 24a are S poles. The direction of magnetization can be reversed in all of the electrodes 21 to 24.

Arranged in the above-described manner, the electrodes 21 to 24, which are magnets, are arranged such that the N-pole surfaces are opposed and parallel to each other and the S-pole surfaces are opposed and parallel to each other. Accordingly, the electrodes 21 to 24 are attracted to each other by their magnetic force. As a result, the electrodes 21 to 24, which are magnets, can be secured onto a center portion 25c of the cross-shaped attracting portion 25 without the use of an adhesive portion such as an adhesive agent.

Between the electrodes 21 to 24, the attracting portion 25 is arranged. The attracting portion 25 is made of an insulating non-magnetic material, for example, resin. The attracting portion 25 has a section shaped like a cross when seen through the end surface 20a along the axial line axd, and, in the attracting portion 25, the center portion 25c is larger than the radial end. Here, the center portion 25c is shaped like a prism. The center portion 25c fills the space between the electrodes 21 to 24.

The attracting portion 25 has an attracting protrusion 25G1 filling the gap G1 between the first electrode 21 and the second electrode 22 and protruding radially outward beyond the outer peripheral surfaces 21a, 22a. The attracting portion 25 has an attracting protrusion 25G2 filling the gap G2 between the first electrode 21 and the third electrode 23 and protruding radially outward beyond the outer peripheral surfaces 21a, 23a.

The attracting portion 25 has an attracting protrusion 25G3 filling the gap G3 between the second electrode 22 and the fourth electrode 24 and protruding radially outward beyond the outer peripheral surfaces 22a, 24a. The attracting portion 25 has an attracting protrusion 25G4 filling the gap G4 between the third electrode 23 and the fourth electrode 24 and protruding radially outward beyond the outer peripheral surfaces 23a, 24a.

When seen in the section transverse the direction along the axial line axd, the attracting protrusions 25G1 to 25G4 are shaped as radially outward extensions of the diagonals of the rectangle (square) formed by the electrodes 21 to 24. The attracting protrusions 25G1 to 25G4 are formed such that they all have the same protruding height in the radial direction. Alternatively, the attracting protrusions 25G1 to 25G4 may be formed such that they have any, for example, different protruding heights in the radial direction. By adjusting the protruding heights of the attracting protrusions 25G1 to 25G4 in the radial direction, the sensitivity of the detection, described below, can be tuned.

The size, in the circumferential direction rtd, of the gaps G1 to G4 between the electrodes 21 to 24 is larger than the size of the conductive substance that can be contained in the lubricating oil. For example, the conductive substance has a size of approximately 1.0 μm to 100 μm. The gaps G1 to G4 are preferably arranged at such intervals that no short circuit is created by the iron powder resulting from initial wear period. The gaps G1 to G4 all have the same size in the circumferential direction rtd.

Between the electrodes 21 to 24, which are magnets, magnetic flux lines run radially outside the attracting protrusions 25G1 to 25G4 to connect the electrodes 21 to 24, as shown in FIG. 9. Between the first electrode 21 and the second electrode 22, magnetic flux lines start from the outer peripheral surface 22a of the second electrode 22, which is the N pole, run radially outside the attracting protrusion 25G1, and proceed toward the outer peripheral surface 21a of the first electrode 21, which is the S pole. Between the first electrode 21 and the third electrode 23, magnetic flux lines start from the outer peripheral surface 23a of the third electrode 23, which is the N pole, run radially outside the attracting protrusion 25G2, and proceed toward the outer peripheral surface 21a of the first electrode 21, which is the S pole.

Between the fourth electrode 24 and the second electrode 22, magnetic flux lines start from the outer peripheral surface 22a of the second electrode 22, which is the N pole, run radially outside the attracting protrusion 25G3, and proceed toward the outer peripheral surface 24a of the fourth electrode 24, which is the S pole. Between the fourth electrode 24 and the third electrode 23, magnetic flux lines start from the outer peripheral surface 23a of the third electrode 23, which is the N pole, run radially outside the attracting protrusion 25G4, and proceed toward the outer peripheral surface 24a of the fourth electrode 24, which is the S pole.

The electrodes 21 to 24 do not need to be in contact with the attracting protrusions 25G1 to 25G4. As shown in FIG. 9, as moving outward radially from the center portion 25c, the spacing distance between the electrodes 21 to 24 and the attracting protrusions 25G1 to 25G4 may increase. The electrodes 21 to 24 can have a non-magnetic conductor portion at a position opposite the end surface 20a. If such is the case, in the electrodes 21 to 24, the magnet and the conductor portion are in contact with each other so that the electrodes 21 to 24 are electrically conductive.

Output lines are connected to the first, second, third and fourth electrodes 21, 22, 23 and 24. The first, second, third and fourth electrodes 21, 22, 23 and 24 are respectively electrically connected to the sensing unit 5 (see FIG. 1 as mentioned in the first embodiment) via the output lines. The electrodes 21 to 24 are insulated from each other. The first electrode 21 and one of the other electrodes 22 to 24 form a pair of electrodes, and the attracting portion 25 arranged between the paired electrodes constitutes a single detecting unit together with the pair of electrodes.

In the present embodiment, the sensor 20 includes three detecting units, corresponding to the second, third and fourth electrodes 22, 23 and 24. There are no particular limitations on the number of the electrodes 22 to 24 and the number of the detecting units. Since the electrodes 21 to 24 of the sensor 20, which are magnets, produce magnetic flux lines between the paired ones of the electrodes 21 to 24, the abrasion powder mp (see FIG. 5 mentioned in the first embodiment) contained in the lubricating oil are attracted by the attracting portion 25. If the conductive particles mp are gathered in the vicinity of the attracting portion 25 in this manner, the detecting units experience a change in electrical resistance. While no conductive particles (abrasion powder) mp are attracted, the detecting units may all exhibit the same electrical resistance.

Through the output lines connected to the electrodes 22 to 24, the detecting units are electrically connected to the sensing unit 5. In the present embodiment, the detecting units corresponding to the second and third electrodes 22 and 23 are connected to each other in parallel. Between the first electrode 21 and the second electrode 22, voltage is applied by the same voltage source. Between the first electrode 21 and the third electrode 23, voltage is applied by the same voltage source. If the conductive particles mp are gathered in the vicinity of the attracting protrusion 25G1, the detecting unit corresponding to the second electrode 22 experiences a change in electrical resistance. If the conductive particles mp are gathered in the vicinity of the attracting protrusion 25G2, the detecting unit corresponding to the third electrode 23 experiences a change in electrical resistance.

The sensing unit 5 is configured to sense a change in electrical resistance between the first electrode 21 and the second electrode 22. The sensing unit 5 includes a sensor drive circuit for predicting a failure of the parts constituting the mechanism 1 based on, for example, a change in electrical resistance caused by the gathering of the conductive particles mp in the vicinity of the attracting protrusion 25G1. If the conductive particles mp contained in the lubricating oil are gathered in the vicinity of the attracting protrusion 25G1, this causes a drop in electrical resistance (or a short circuit) between the first electrode 21 and the second electrode 22 to which voltage is being applied, resulting in a change in output level of the output lines. The sensing unit 5 senses such a change in electrical resistance, thereby predicting a failure of the parts constituting the mechanism 1.

Likewise, the sensing unit 5 is configured to sense a change in electrical resistance between the first electrode 21 and the third electrode 23. The sensing unit 5 includes a sensor drive circuit for predicting a failure of the parts constituting the mechanism 1 based on, for example, a change in electrical resistance caused by the gathering of the conductive particles mp in the vicinity of the attracting protrusion 25G2. If the conductive particles mp contained in the lubricating oil are gathered in the vicinity of the attracting protrusion 25G3, this causes a drop in electrical resistance (or a short circuit) between the first electrode 21 and the third electrode 23 to which voltage is being applied, resulting in a change in output level of the output lines. The sensing unit 5 senses such a change in electrical resistance, thereby predicting a failure of the parts constituting the mechanism 1.

Between the first electrode 21 and the fourth electrode 24, voltage is applied by the same voltage source. If the conductive particles mp are gathered in the vicinity of both of the attracting protrusions 25G1 and 25G3, the detecting unit corresponding to the fourth electrode 24 experiences a change in electrical resistance. If the conductive substance is gathered in the vicinity of both of the attracting protrusions 25G2 and 25G4, the detecting unit corresponding to the fourth electrode 24 experiences a change in electrical resistance.

The sensing unit 5 is configured to sense a change in electrical resistance between the first electrode 21 and the fourth electrode 24. The sensing unit 5 includes a sensor drive circuit for predicting a failure of the parts constituting the mechanism 1 based on, for example, a change in electrical resistance caused by the gathering of the conductive particles mp in the vicinity of the attracting protrusions 25G1 and 25G3. If the conductive particles mp contained in the lubricating oil are gathered in the vicinity of both of the attracting protrusions 25G1 and 25G3, this causes a drop in electrical resistance (or a short circuit) between the first electrode 21 and the fourth electrode 24 to which voltage is being applied, resulting in a change in output level of the output lines. The sensing unit 5 senses such a change in electrical resistance, thereby predicting a failure of the parts constituting the mechanism 1. This sensing is not made possible until the conductive particles mp are gathered in the vicinity of both of the attracting protrusions 25G1 and 25G3.

Likewise, the sensing unit 5 includes a sensor drive circuit for predicting a failure of the parts constituting the mechanism 1 based on, for example, a change in electrical resistance caused by the gathering of the conductive particles mp in the vicinity of the attracting protrusions 25G2 and 25G4. If the conductive particles mp contained in the lubricating oil are gathered in the vicinity of both of the attracting protrusions 25G2 and 25G4, this causes a drop in electrical resistance (or a short circuit) between the first electrode 21 and the fourth electrode 24 to which voltage is being applied, resulting in a change in output level of the output lines. The sensing unit 5 senses such a change in electrical resistance, thereby predicting a failure of the parts constituting the mechanism 1. This sensing is not made possible until the conductive particles mp are gathered in the vicinity of both of the attracting protrusions 25G2 and 25G4.

As described above, the change in electrical resistance experienced by the detecting unit corresponding to the second electrode 22 and the detecting unit corresponding to the third electrode 23 is used to detect a change in electrical resistance in one attracting protrusion, which is selected from the attracting protrusions 25G1 and 25G2. On the other hand, the change in electrical resistance experienced by the detecting unit corresponding to the fourth electrode 24 is used to detect the change in electrical resistance in two attracting protrusions, which are either the attracting protrusions 25G1 and 25G3 or attracting protrusions 25G2 and 25G4. This means that the plurality of detecting units are capable of sensing different conditions. In other words, the detecting units are configured to detect a change in electrical resistance in two stages. The detecting units can perform the sensing in two stages and two systems. Accordingly, the reliability of the failure prediction can be improved.

The sensing unit 5 outputs a signal when a designated one of the detecting units experiences a change in electrical resistance. For example, the sensing unit 5 may be configured to output a signal to a higher-level control device such as a manipulator when two of the detecting units, more specifically, the detecting unit corresponding to the second electrode 22 and the detecting unit corresponding to the third electrode 23 experience a drop in electrical resistance. The sensing unit 5 may be alternatively configured to output a signal when all of the detecting units including the detecting unit corresponding to the fourth electrode 24 experience a drop in electrical resistance.

The drop in electrical resistance may be indicated by an ON signal and an OFF signal corresponding to electrical disconnection and connection. The sensing unit 5 may sense two states of electrical disconnection and connection (hereinafter, may be referred to as "perform digital sensing"). The sensing unit 5 may be connected to a higher-level control device (not shown) such as a manipulator in a wired or wireless manner. The higher-level control device may be configured to, upon reception of a signal from the sensing unit 5, issue an alert for demanding maintenance of, for example, the speed reducer 2 with a predetermined notifying device (for example, a display or voice output device).

As described above, the sensor 20 of the present embodiment includes the plurality of detecting units, and the sensing unit 5 outputs a signal when designated one or more of detecting units experience a drop in electrical resistance. In this way, the sensing unit 5 can be configured to output no signal when just one of the detecting units experiences a change in electrical resistance caused by initial abrasion powder but the other detecting units do not experience a change in electrical resistance. Accordingly, the sensor can be prevented from operating unexpectedly. Furthermore, in the sensor 20, the sensing unit 5 can be configured to output a signal under a designated condition. Therefore, the single sensor 20 can be configured to output a signal in a timely and optimal manner for individual users, who have different requests for failure prediction timing.

While no conductive particles mp are attracted, the detecting units can exhibit the same electrical resistance. This can lower the voltage to be applied to the sensor 20. The detecting units are connected in parallel to each other. This can lower the voltage applied between the paired electrodes in each detecting unit. The sensor 20 is preferably positioned such that the first electrode 21, which forms the detecting unit with all of the other electrodes 22 to 24, deals with a large amount of conductive particles mp.

According to the sensor 20 relating to the present embodiment, the gaps G1 to G4 for detecting the conductive particles mp are arranged next to each other in the circumferential direction rtd along the outer peripheral surfaces 21a to 24a. In this way, when compared with the case where such gaps for detecting conductive particles are arranged next to each other in the radial direction on the end surface 20a of the sensor 20, the sensor 20 can be reduced in size without compromising the detection sensitivity. In addition, the direction of the detection performed by the detecting units can be configured to extend in the circumferential direction rtd along the outer peripheral surfaces 21a to 24a. Accordingly, when compared with the case where a plurality of detection gaps extending in the axial line axd are arranged next to each other in the circumferential direction of the sensor, the sensor 20 can be reduced in size without compromising the detection sensitivity. Since the magnetic flux lines produced by the electrodes 21 to 24, which are magnets, start from the position immediately close to the attracting portion 25 and run radially, the conductive particles mp can be attracted highly efficiently. Thus, the size reduction can not result in lower attraction efficiency. As a result, the size reduction can carry on. Furthermore, the sensor 20 of the present embodiment can be constituted by a reduced number of parts, assembled easily and manufactured at a reduced cost as reasonable plate-shaped magnets are employed.

Figure 10:
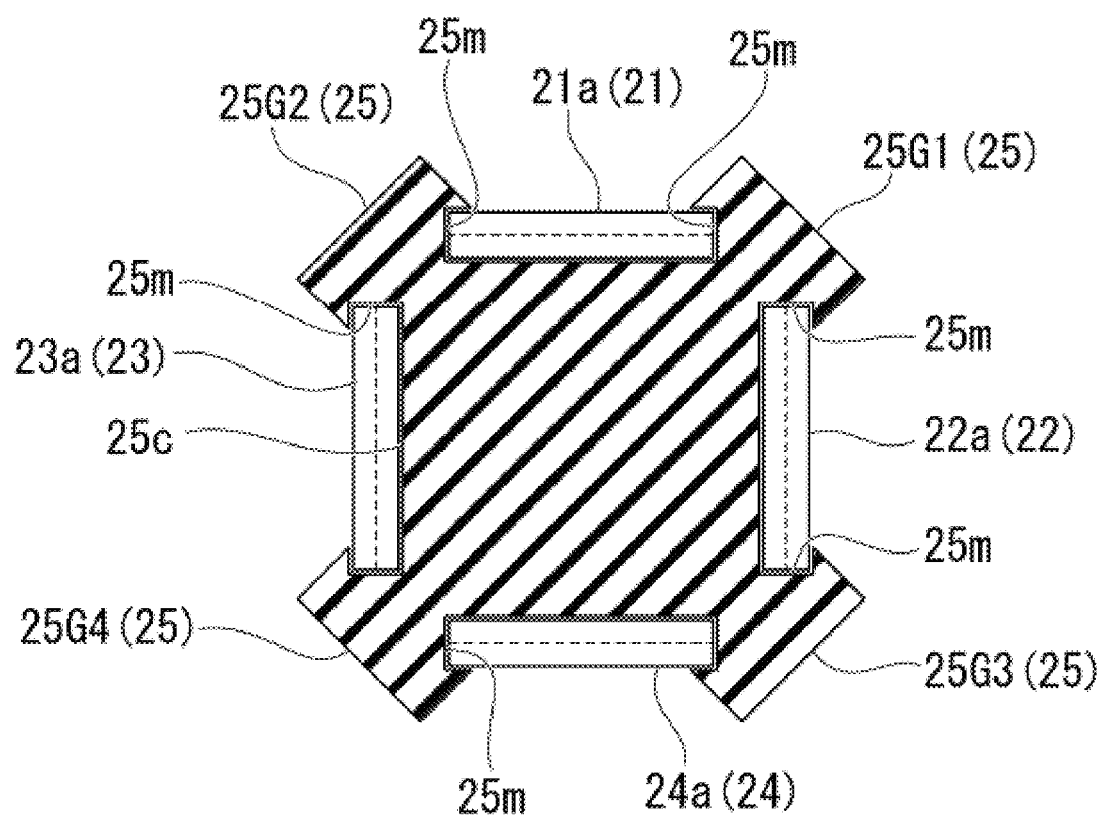
FIG. 10 shows a section orthogonal to the axial direction in order to illustrate another example of the sensor relating to the second embodiment of the present invention.

FIG. 10 shows a section orthogonal to the axial direction in order to illustrate another example of the sensor relating to the present embodiment. In the sensor 20 relating to the present embodiment, the magnets forming the electrodes 21 to 24 are partly spaced away from the attracting protrusions 25G1 to 25G4. As shown in FIG. 10, however, grooves 25m may be provided in the bases of the attracting protrusions 25G1 to 25G4 and the center portion 25c for receiving the magnets forming the electrodes 21 to 24. In this case, the grooves 25m preferably do not cover the outer peripheral surfaces 21a to 24a of the electrodes 21 to 24.

Irrespective of whether there are the grooves 25m or not, the same amount of conductive particles mp can preferably gather, which is determined by the total length in the circumferential direction rtd of the attracting protrusions 25G1 to 25G4, namely, in the example case of the attracting protrusion 25G1, the surface distance from the adjacent outer peripheral surface 21a to the outer peripheral surface 22a. In this way, the detection sensitivity of each detecting unit can be designated independent from whether there are the grooves 25m. At the same time, irrespective of whether there are the grooves 25m or not, the size in the circumferential direction rtd of the gaps G1 to G4 preferably remains the same.

In the present example, the sensor 20 can be easily assembled by inserting into the grooves 25m the electrodes 21 to 24 along the axial line axd direction from the end surface 20a side. With this configuration, the electrodes 21 to 24 can be more rigidly secured than when the electrodes 21 to 24 are secured onto the attracting portion 25 only through the magnetic force of the electrodes 21 to 24.

Figure 11:
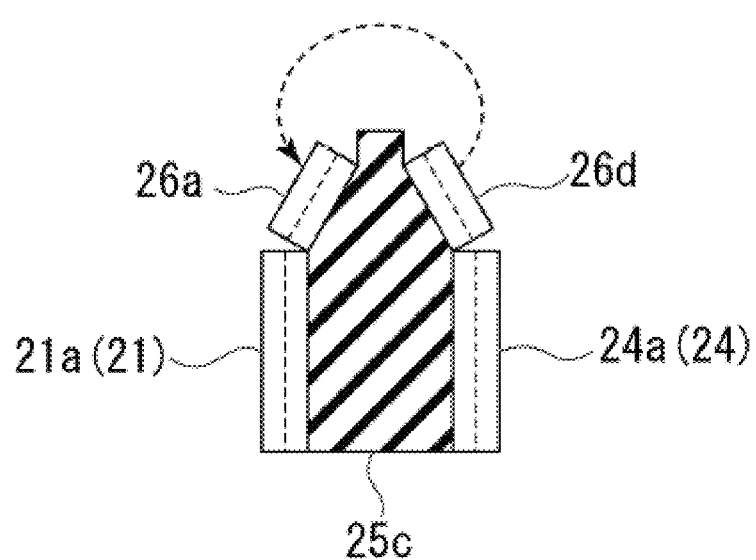
FIG. 11 shows a section along the axial direction in order to illustrate another example of the sensor relating to the second embodiment of the present invention.

FIG. 11 shows a section along the axial direction in order to illustrate another example of the sensor relating to the present embodiment. In the sensor 20 relating to the present embodiment, the electrodes 21 to 24 and the attracting portion 25 are flush with each other on the end surface 20a. As shown in FIG. 11, however, an end surface 20d can be formed as an inclined surface the central portion of which protrudes outward in the axial line axd direction and electrodes 26a to 26d, which are magnets, can be provided. In this case, the electrodes 26a to 26d and electrodes 21 to 24 are also arranged such that adjacent ones of the magnets are different poles.

With such configurations, in the end surface 20a, which is a plane orthogonal to the axial line axd, weak magnetic flux lines leaking from the magnets forming the electrodes 21 to 24 can form further detecting units together with the strong magnetic flux line produced by the electrodes 26a to 26d. In this way, the reliability and sensitivity of the detection performed by the sensor 20 can be set at a predetermined level.

In the sensor 20 relating to the present embodiment, the output lines extending from the electrodes 21 to 24 can be also formed by using the flexible substrates 11f to 14f, as shown in FIG. 7 mentioned in the first embodiment. In this case, the electrodes 21 to 24, which are magnets, are arranged such that the N-pole surface is opposed and parallel to the S-pole surface. Accordingly, the flexible substrates 11f to 14f are pressed against the attracting portion 25 with stronger force than in the first embodiment. This can in turn allow the flexible substrates 11f to 14f to be more rigidly secured and contribute to maintain excellent contact.

Figure 12:
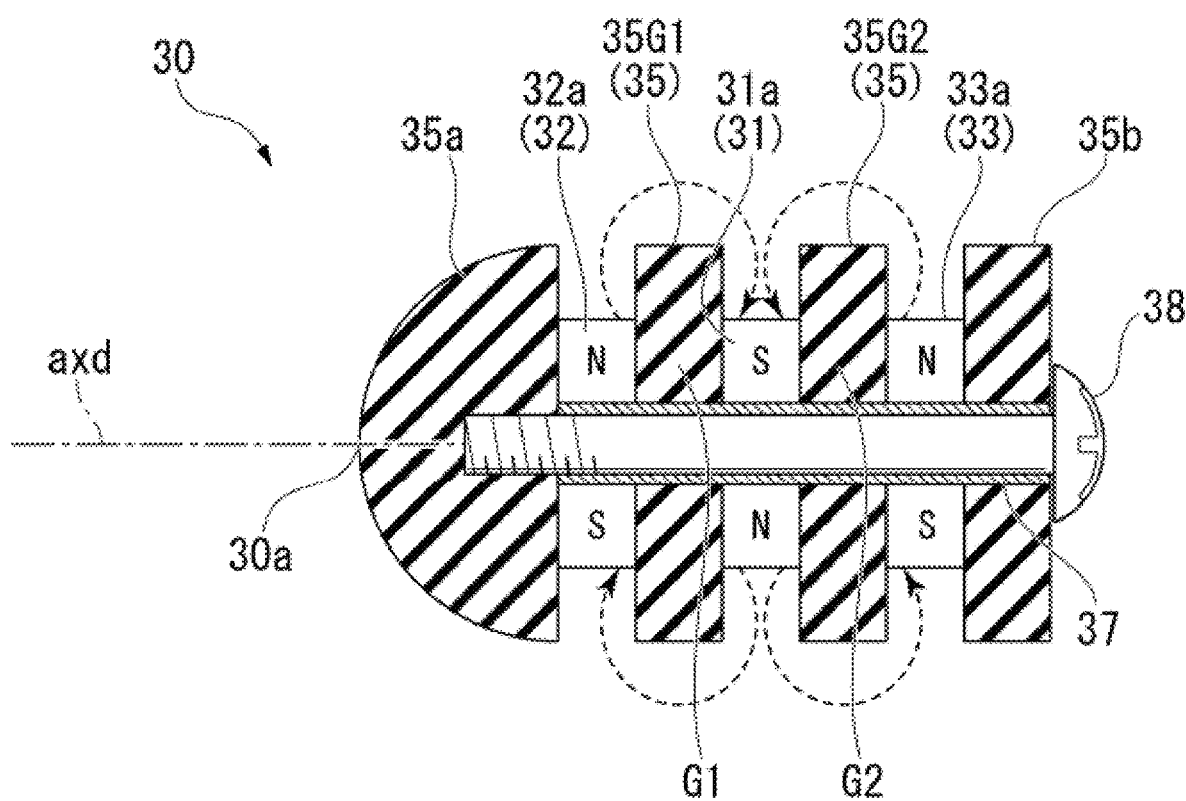
FIG. 12 is a sectional view taken along the axial direction and showing a sensor relating to a third embodiment of the present invention.
Figure 13:
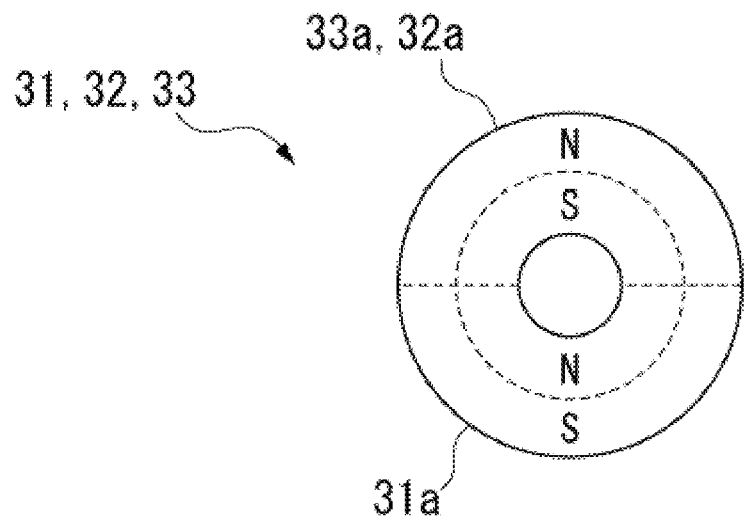
FIG. 13 shows magnets included in the sensor relating to the third embodiment of the present invention.

The following describes a sensor relating to a third embodiment of the present invention with reference to the drawings. FIG. 12 is a sectional view taken along the axial direction and showing the sensor relating to the third embodiment of the present invention. FIG. 13 is used to illustrate the magnets of the sensor relating to the present embodiment. In FIG. 12, the reference numeral 30 denotes the sensor. The third embodiment is different from the above-described first embodiment in terms of the configurations of the sensor. The constituents of the mechanism 1 illustrated in FIG. 1 are not described here.

As shown in FIG. 12, the sensor 30 has a substantially cylindrical outer shape around an axial line axd. The sensor 30 includes a first electrode 31, a second electrode 32, a third electrode 33, and an attracting portion (catching portion) 35.

A front end 30a of the sensor 30 is substantially shaped like a hemisphere. The first, second and third electrodes 31, 32 and 33 are plate members having a circular outline centered around the axial line axd when seen in the axial line axd direction. The first, second and third electrodes 31, 32 and 33 all have substantially the same outline and substantially the same thickness. The second electrode 32, the first electrode 31 and the third electrode 33 are stacked in the axial line axd direction in the stated order from the front end 30a toward the base end along the axial line axd direction.

The second electrode 32, first electrode 31 and third electrode 33 are arranged next to each other in the direction along the axial line axd and parallel to each other concentrically. The second electrode 32, first electrode 31 and third electrode 33 are arranged such that their respective outer peripheral surfaces 31a to 33a form the same or flush cylindrical surface. The second electrode 32, first electrode 31 and third electrode 33 all have the same radial size in the direction orthogonal to the axial line axd.

The second electrode 32, first electrode 31 and third electrode 33 are spaced away from each other in the direction along the axial line axd. Gaps G1 and G2 are formed between the electrodes 31 to 33. The gap G1 denotes the spacing distance in the direction along the axial line axd between the first electrode 31 and the second electrode 32. The gap G2 denotes the spacing distance in the direction along the axial line axd between the first electrode 31 and the third electrode 33.

The first, second and third electrodes 31, 32 and 33 are all magnets. The magnets are, for example, permanent magnets. In all of the first, second and third electrodes 31, 32 and 33, the direction of magnetization extends in the radial direction of the sensor 30. The first electrode 31 is magnetized such that the halves of the radially outer peripheral surface 31a are different poles. Likewise, the second and third electrodes 32 and 33 are both magnetized such that the halves of their respective outer peripheral surfaces 32a and 33a are different poles.

The poles of the outer peripheral surface 31a of the first electrode 31 are opposite to the poles of the outer peripheral surfaces 32a and 33a of the second and third electrodes 32 and 33. In other words, the electrodes 31, 32, 33, which are adjacent to each other along the axial line axd, are magnetized such that different poles are adjacent. That is to say, the first electrode 31 is a magnet magnetized in the same manner as the second and third electrodes 32 and 33 but rotated around the axial line axd by 180°.

For example, as shown in FIG. 12, the first electrode 31 is magnetized such that the lower half of the outer peripheral surface 31a is the N pole. The second and third electrodes 32 and 33 are magnetized such that the upper half of their respective outer peripheral surfaces 32a and 33a is the N pole. The direction of magnetization can be reversed in all of the electrodes 31 to 33.

Arranged in the above-described manner, the electrodes 31 to 33, which are magnets, are attracted to each other in the axial line axd direction by their magnetic force. As a result, the electrodes 31 to 33 can be arranged to overlap each other in the axial line axd direction and secured onto the attracting portion 25 without the use of an adhesive portion such as an adhesive agent.

Between the electrodes 31 to 33, the attracting portion 35 is arranged. The attracting portion 35 is made of an insulating non-magnetic material, for example, resin. The attracting portion 35 is a plate-shaped member having a circular outline when seen along the axial line axd from the side of the front end 30a.

The attracting portion 35 has an attracting protrusion 35G1 filling the gap G1 between the first electrode 31 and the second electrode 32 and protruding radially outward beyond the outer peripheral surfaces 31a, 32a. The attracting portion 35 has an attracting protrusion 35G2 filling the gap G2 between the first electrode 31 and the third electrode 33 and protruding radially outward beyond the outer peripheral surfaces 31a, 33a.

The attracting protrusions 35G1 and 35G2 are formed such that they both have the same protruding height beyond the outer peripheral surfaces 31a to 33a in the radial direction. Alternatively, the attracting protrusions 35G1, 35G2 may be formed such that they have any, for example, different protruding heights in the radial direction. By adjusting the protruding heights of the attracting protrusions 35G1 and 35G2 in the radial direction, the sensitivity of the detection, described below, can be tuned.

The thickness, in the axial line axd direction, of the gaps G1 and G2 between the electrodes 31 to 33 is larger than the size of the conductive substance that can be contained in the lubricating oil. For example, the conductive substance has a size of approximately 1.0 μm to 100 μm. The gaps G1 and G2 are preferably arranged at such intervals that no short circuit is created by the iron powder resulting from initial wear period. The gaps G1 and G2 have the same size in the direction along the axial line axd.

Between the electrodes 31 to 33, which are magnets, magnetic flux lines run radially outside the attracting protrusions 35G1, 35G2 to connect the electrodes 31 to 33 in the direction along the axial line axd, as shown in FIG. 12. As shown in the lower part of FIG. 12, between the first electrode 31 and the second electrode 32, magnetic flux lines start from the outer peripheral surface 31a of the first electrode 31, which is the N pole, run radially outside the attracting protrusion 35G1, and proceed toward the outer peripheral surface 32a of the second electrode 32, which is the S pole. At the same time, as shown in the upper part of FIG. 12, between the first electrode 31 and the second electrode 32, magnetic flux lines start from the outer peripheral surface 32a of the second electrode 32, which is the N pole, run radially outside the attracting protrusion 35G1, and proceed toward the outer peripheral surface 31a of the first electrode 31, which is the S pole.

As shown in the lower part of FIG. 12, between the first electrode 31 and the third electrode 33, magnetic flux lines start from the outer peripheral surface 31a of the first electrode 31, which is the N pole, run radially outside the attracting protrusion 35G2, and proceed toward the outer peripheral surface 33a of the third electrode 33, which is the S pole. At the same time, as shown in the upper part of FIG. 12, between the first electrode 31 and the third electrode 33, magnetic flux lines start from the outer peripheral surface 33a of the third electrode 33, which is the N pole, run radially outside the attracting protrusion 35G2, and proceed toward the outer peripheral surface 31a of the first electrode 31, which is the S pole.

Outside the second electrode 32 in the direction along the axial line axd, in other words, on the front end 30a, a front end portion 35a made of the same material as the attracting portion 35 is formed. The front end portion 35a has the same outline as the attracting protrusions 35G1, 35G2 when seen in the direction along the axial line axd. The front end portion 35a has a spherical surface. Outside the third electrode 33 in the direction along the axial line axd, in other words, near the base of the sensor 30, a base end portion 35*b* made of the same material as the attracting portion 35 is formed. The base end portion 35*b* has the same outline as the attracting protrusions 35G1, 35G2 when seen in the direction along the axial line axd. The base end portion 35*b* has the same thickness as the attracting protrusions 35G1, 35G2 in the direction along the axial line axd.

The base end portion 35*b*, the third electrode 33, the attracting protrusion 35G2, the first electrode 31, the attracting protrusion 35G1 and the second electrode 32, which are stacked on each other along the axial line axd, all have a center hole through which a fastening member 38 (in the illustrated embodiment, a screw) is inserted and centered around the axial line axd. The fastening member 38 is inserted through the center holes centered around the axial line axd, so that the electrodes 31 to 33, the attracting protrusions 35G1, 35G2, the front end portion 35*a* and the base end portion 35*b* are secured to each other. A tube 37 is provided radially outside the screw 38 and surrounds the screw 38. The tube 37 contributes to keep the electrodes 31 to 33 and the screw 38 insulated from each other and to secure the electrodes 31 to 33 and attracting protrusions 35G1, 35G2 relative to the front and base end portions 35*a*, 35*b* at predetermined positions in the radial direction.

Figure 14:
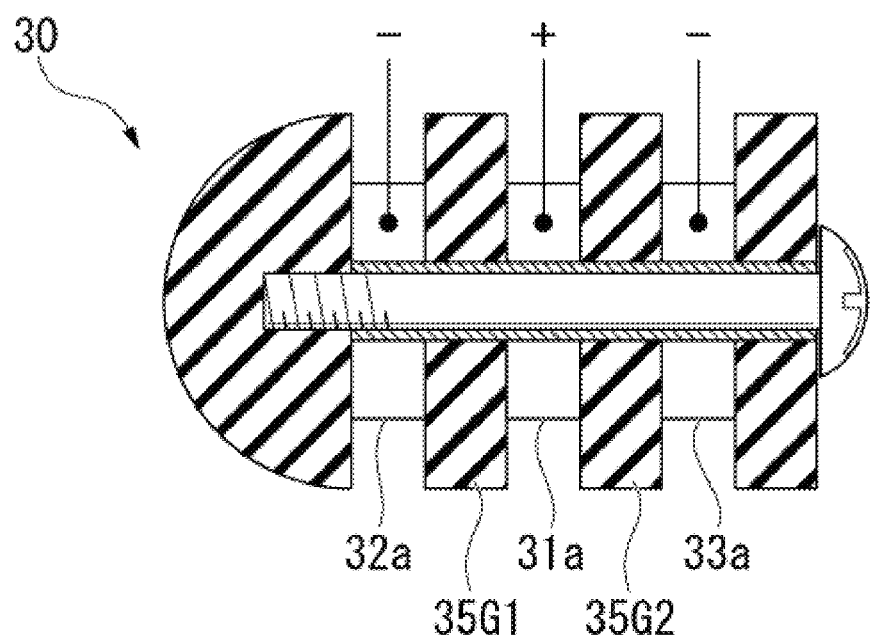
FIG. 14 shows how the electrodes are arranged in the sensor relating to the third embodiment of the present invention.

Output lines are connected to the first, second and third electrodes 31, 32 and 33. The first, second and third electrodes 31, 32 and 33 are respectively electrically connected to the sensing unit 5 (see FIG. 1) via the output lines. The electrodes 31 to 33 are insulated from each other. The first electrode 31 and one of the other electrodes 32 to 33 form a pair of electrodes, and the attracting portion 35 arranged between the paired electrodes constitutes a single detecting unit together with the pair of electrodes. In FIG. 14, the electrode pairs constituting the detecting units are denoted by assigning the sign "+" to the output line of the first electrode 31 and "−" to the output lines of the other electrodes 32, 33.

Figure 15:
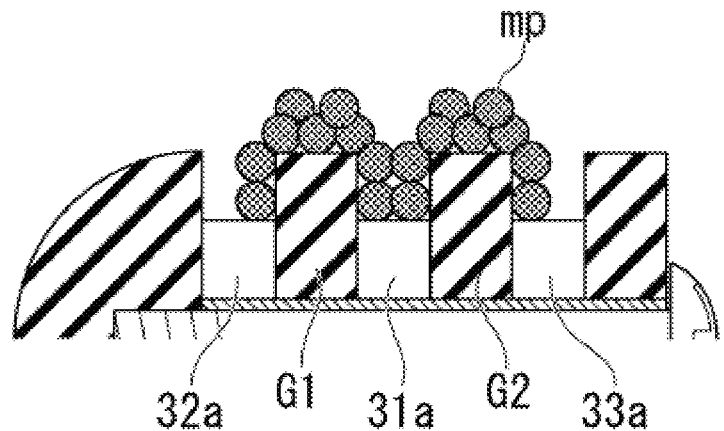
FIG. 15 is a sectional view showing how detection is performed in the sensor relating to the third embodiment of the present invention.

FIG. 15 is a sectional view showing how detection is performed in the sensor relating to the present embodiment. In the present embodiment, the sensor 30 includes two detecting units, corresponding to the second and third electrodes 32, 23. There are no particular limitations on the number of the electrodes 32 to 33 and the number of the detecting units. Since the electrodes 31 to 33 of the sensor 30, which are magnets, produce magnetic flux lines between the paired ones of the electrodes 31 to 33, the conductive particles (abrasion powder) mp contained in the lubricating oil are attracted by the attracting portion 35, as shown in FIG. 15. If the conductive particles mp are gathered in the vicinity of the attracting portion 35 in this manner, the detecting units experience a change in electrical resistance. While no conductive particles (abrasion powder) mp are attracted, the detecting units may exhibit the same electrical resistance.

In the present embodiment, the detecting units corresponding to the second and third electrodes 32 and 33 are connected to each other in parallel. Between the first electrode 31 and the second electrode 32, voltage is applied by the same voltage source. Between the first electrode 31 and the third electrode 33, voltage is applied by the same voltage source. If the conductive particles mp are gathered in the vicinity of the attracting protrusion 35G1, the detecting unit corresponding to the second electrode 32 experiences a change in electrical resistance. If the conductive particles mp are gathered in the vicinity of the attracting protrusion 35G2, the detecting unit corresponding to the third electrode 33 experiences a change in electrical resistance.

The sensing unit 5 is configured to sense a change in electrical resistance between the first electrode 31 and the second electrode 32. The sensing unit 5 includes a sensor drive circuit for predicting a failure of the parts constituting the mechanism 1 based on, for example, a change in electrical resistance caused by the gathering of the conductive particles mp in the vicinity of the attracting protrusion 35G1. If the conductive particles mp contained in the lubricating oil are gathered in the vicinity of the attracting protrusion 35G1, this causes a drop in electrical resistance (or a short circuit) between the first electrode 31 and the second electrode 32 to which voltage is being applied, resulting in a change in output level of the output lines. The sensing unit 5 senses such a change in electrical resistance, thereby predicting a failure of the parts constituting the mechanism 1.

Likewise, the sensing unit 5 is configured to sense a change in electrical resistance between the first electrode 31 and the third electrode 33. The sensing unit 5 includes a sensor drive circuit for predicting a failure of the parts constituting the mechanism 1 based on, for example, a change in electrical resistance caused by the gathering of the conductive particles mp in the vicinity of the attracting protrusion 35G2. If the conductive particles mp contained in the lubricating oil are gathered in the vicinity of the attracting protrusion 35G2, this causes a drop in electrical resistance (or a short circuit) between the first electrode 31 and the third electrode 33 to which voltage is being applied, resulting in a change in output level of the output lines. The sensing unit 5 senses such a change in electrical resistance, thereby predicting a failure of the parts constituting the mechanism 1.

As described above, the change in electrical resistance experienced by the detecting unit corresponding to the second electrode 32 and the detecting unit corresponding to the third electrode 33 is used to detect a change in electrical resistance in one attracting protrusion, which is selected from the attracting protrusions 35G1 and 35G2. This means that the plurality of detecting units are capable of sensing different conditions. In other words, the detecting units are configured to detect a change in electrical resistance in two systems.

The sensing unit 5 outputs a signal when designated one or more of the detecting units experiences a change in electrical resistance. For example, the sensing unit 5 may be configured to output a signal to a higher-level control device such as a manipulator when two or more of the detecting units experience a drop in electrical resistance, or configured to output a signal when all of the detecting units experience a drop in electrical resistance.

The drop in electrical resistance may be indicated by an ON signal and an OFF signal corresponding to electrical disconnection and connection. The sensing unit 5 may sense two states of electrical disconnection and connection (hereinafter, may be referred to as "perform digital sensing"). The sensing unit 5 may be connected to a higher-level control device (not shown) such as a manipulator in a wired or wireless manner. The higher-level control device may be configured to, upon reception of a signal from the sensing unit 5, issue an alert for demanding maintenance of, for example, the speed reducer 2 with a predetermined notifying device (for example, a display or voice output device).

As described above, the sensor 30 of the present embodiment includes the plurality of detecting units, and the sensing unit 5 outputs a signal when designated one or more of the detecting units experience a drop in electrical resistance. In this way, the sensing unit 5 can be configured to output no signal when just one of the detecting units experiences a change in electrical resistance caused by initial abrasion powder but the other detecting units do not experience a change in electrical resistance. Accordingly, the sensor can be prevented from operating unexpectedly. Furthermore, in the sensor 30, the sensing unit 5 can be configured to output a signal under a designated condition. Therefore, the single sensor 30 can be configured to output a signal in a timely and optimal manner for individual users, who have different requests for failure prediction timing.

While no conductive particles mp are attracted, the detecting units can exhibit the same electrical resistance. This can lower the voltage to be applied to the sensor 30. The detecting units are connected in parallel to each other. This can lower the voltage applied between the paired electrodes in each detecting unit. The sensor 30 is preferably positioned such that the first electrode 31, which forms the detecting unit with every one of the other electrodes 32, 33, deals with a large amount of conductive particles mp.

According to the sensor 30 relating to the present embodiment, the gaps G1, G2 for detecting the conductive particles mp extend along the outer peripheral surfaces 31a to 33a and are arranged next to each other in the direction along the axial line axd. In this way, when compared with the case where such gaps for detecting conductive particles are arranged next to each other in the radial direction on the end surface of the sensor 30, the sensor 30 can be reduced in size without compromising the detection sensitivity. In addition, the detecting units extending along the outer peripheral surfaces 31a to 33a can be adjacent to each other in the direction along the axial line axd and the direction of the detection can be configured to extend in the direction along the axial line axd. Accordingly, when compared with the case where a plurality of detection gaps extending in the axial line axd direction are arranged next to each other in the circumferential direction of the sensor, the sensor can be reduced in size without compromising the detection sensitivity. Since the magnets are exposed on the surface of the sensor, the magnets also serve as the electrodes 31 to 33, and the magnetic flux lines start from the position immediately close to the attracting portion 35 and run radially, the conductive particles mp can be attracted highly efficiently. Thus, the size reduction can not result in lower attraction efficiency. Furthermore, the sensor 30 of the present embodiment can be constituted by a reduced number of parts, assembled easily and manufactured at a reduced cost.

Figure 16:
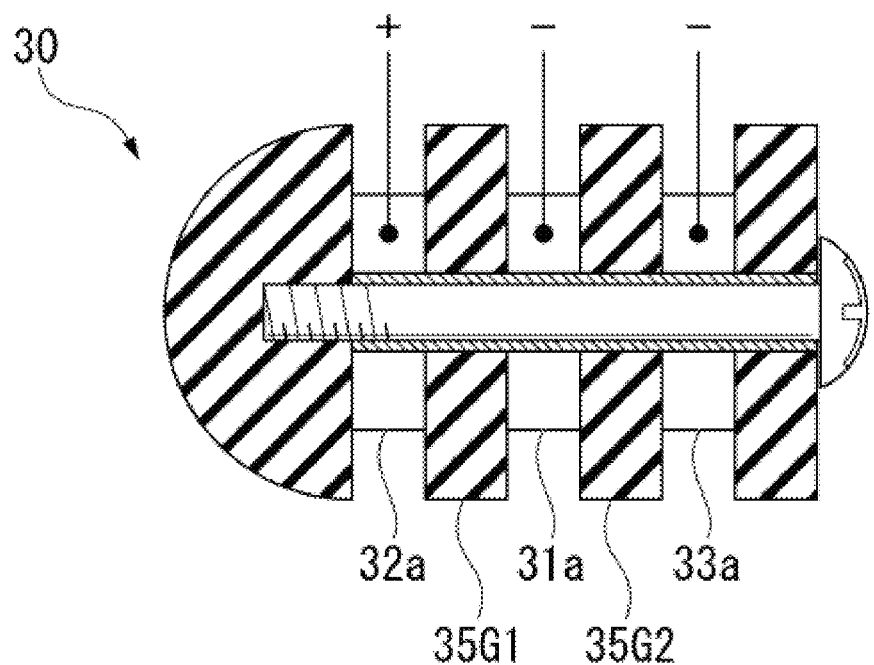
FIG. 16 shows a section along the axial direction in order to illustrate another example of the sensor relating to the third embodiment of the present invention.

FIG. 16 shows another example of the sensor relating to the present embodiment. In the sensor 30 relating to the present embodiment, the detecting units corresponding to the electrodes 31 to 33 constitute two parallel systems. As shown in FIG. 16, however, the detecting units can alternatively form two stages.

Specifically, the second electrode 32 near the front end 30a and the first electrode 31 positioned at the center in the axial line axd direction constitute a first-stage detecting unit. The second electrode 32 near the front end 30a and the third electrode 33 at the opposite position in the axial line axd direction constitute a second-stage detecting unit. In FIG. 16, the electrode pairs constituting the detecting units are denoted by assigning the sign "+" to the output line of the second electrode 32 and "−" to the output lines of the other electrodes 31, 33.

In this example, the sensing unit 5 is configured to sense a change in electrical resistance between the second electrode 32 and the first electrode 31. If the conductive particles mp contained in the lubricating oil in the mechanism 1 are gathered in the vicinity of the attracting protrusion 15G1, this causes a drop in electrical resistance (or a short circuit) between the second electrode 32 and the first electrode 31 to which voltage is being applied, resulting in a change in output level of the output lines. The sensing unit 5 senses such a change in electrical resistance, thereby predicting a failure of the parts constituting the mechanism 1.

In the present example, the sensing unit 5 predicts a failure of the parts constituting the mechanism 1 based on, for example, a change in electrical resistance caused by the gathering of the conductive particles mp in the vicinity of the attracting protrusions 35G1 and 35G2. If the conductive particles mp contained in the lubricating oil are gathered in the vicinity of both of the attracting protrusions 35G1 and 35G2, this causes a drop in electrical resistance (or a short circuit) between the second electrode 32 and the third electrode 33 to which voltage is being applied, resulting in a change in output level of the output lines. The sensing unit 5 senses such the change in electrical resistance, thereby predicting a failure of the parts constituting the mechanism 1. This sensing is not made possible until the conductive particles mp are gathered in the vicinity of both of the attracting protrusions 35G1 and 35G2.

As described above, the change in electrical resistance experienced by the detecting unit corresponding to the first electrode 31 is used to detect a change in electrical resistance in one attracting protrusion, which is the attracting protrusion 35G1. On the other hand, the change in electrical resistance experienced by the detecting unit corresponding to the third electrode 33 is used to detect the change in electrical resistance in two attracting protrusions, which are the attracting protrusions 35G1 and 35G2. This means that the plurality of detecting units are capable of sensing different conditions. In other words, the sensing units are configured to detect a change in electrical resistance in two stages. Accordingly, the reliability of the failure prediction can be improved.

For the second electrode 32, the first electrode 31 and the third electrode 33, which are arranged next to each other in the axial line axd direction, FIG. 14 shows the detecting unit configuration "−" "+" "−" and FIG. 16 shows "+" "−" "−." It is, however, possible to provide for detecting unit configuration "−" "−" "+."

Figure 17:
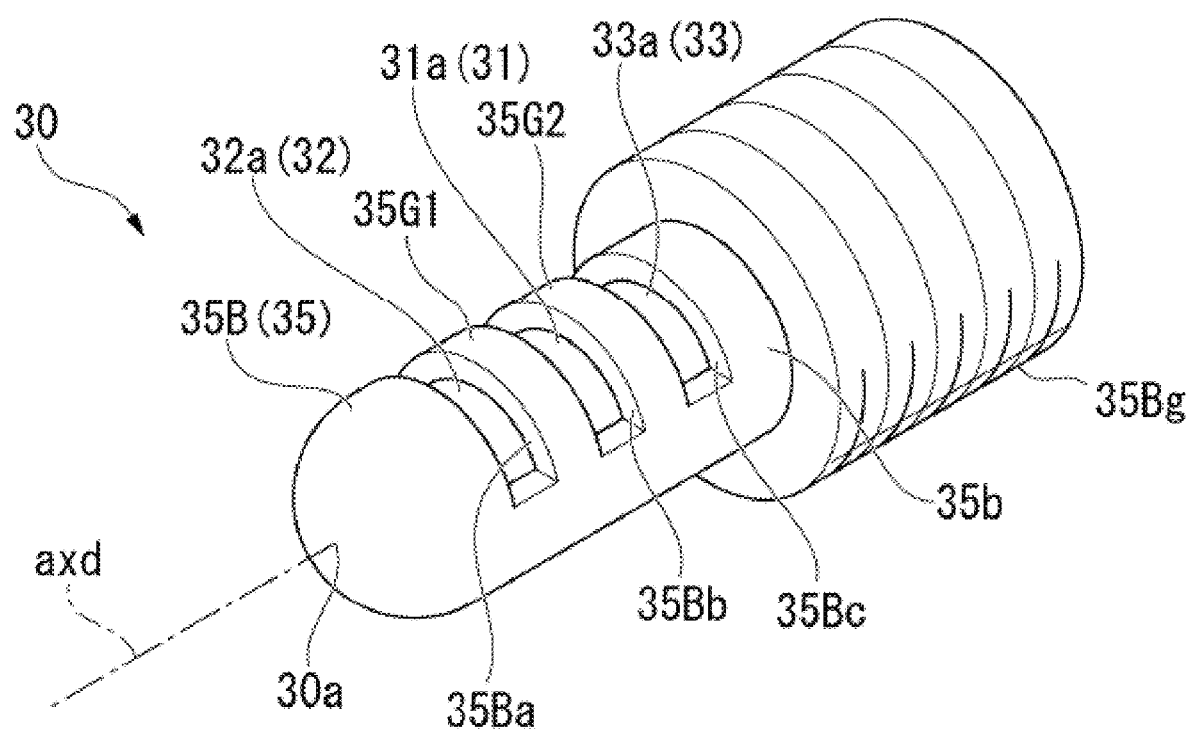
FIG. 17 is a perspective view showing a sensor relating to a fourth embodiment of the present invention.

The following describes a sensor relating to a fourth embodiment of the present invention with reference to the drawings. FIG. 17 is a perspective view showing the sensor relating to the fourth embodiment. The fourth embodiment is different from the above-described third embodiment in terms of the shape of the attracting portion. The common constituents are assigned with the same reference numerals and are not described here.

In the sensor 30 relating to the present embodiment, as shown in FIG. 17, the attracting portion 35 covers a circumferential portion of the electrodes 31 to 33. More specifically, the attracting protrusions 35G1, 35G2, which serve as the gaps G1, G2, correspond to approximately half in the circumferential direction of the electrodes 31 to 33, and the remaining circumferential portion of the electrodes 31 to 33 is covered with the same resin as the resin forming the attracting portion 35. In other words, the attracting portion 35 includes a substantially cylindrical casing 35B. The casing 35B has window portions 35Ba to 35Bc exposing an approximately half of the outer peripheral surfaces 31a to 33a of the electrodes 31 to 33.

The window portions 35Ba to 35Bc are positioned at the same position in the circumferential direction rtd when the sensor 30 is seen in the axial line axd direction. The electrodes 31 to 33, which are magnets, have a region in which the N pole abuts the S pole. The casing 35B having the window portions 35Ba to 35Bc can cover such boundary regions, which are shown in FIG. 13 on the left and right sides. This can prevent erroneous detection that can be attributed to the magnetic flux lines that run circumferentially behind the electrodes 31 to 33 and do not interact with the gaps G1, G2.

The casing 35B can be provided with a screw portion 35Bg having a larger diameter, which is positioned next to the base end portion 35b in the axial line axd direction. For example, the screw portion 35Bg enables the sensor 30 to be secured onto the flange 3 without the use of the support member 2e (see FIG. 1). The screw portion 35Bg is concentrically arranged with the casing 35B and extends in the axial line axd direction from the casing 35B. The screw portion 35Bg and the casing 35B can be integrally shaped.

The sensor 30 relating to the present embodiment can produce the same effects as the above-described third embodiment.

Figure 18:
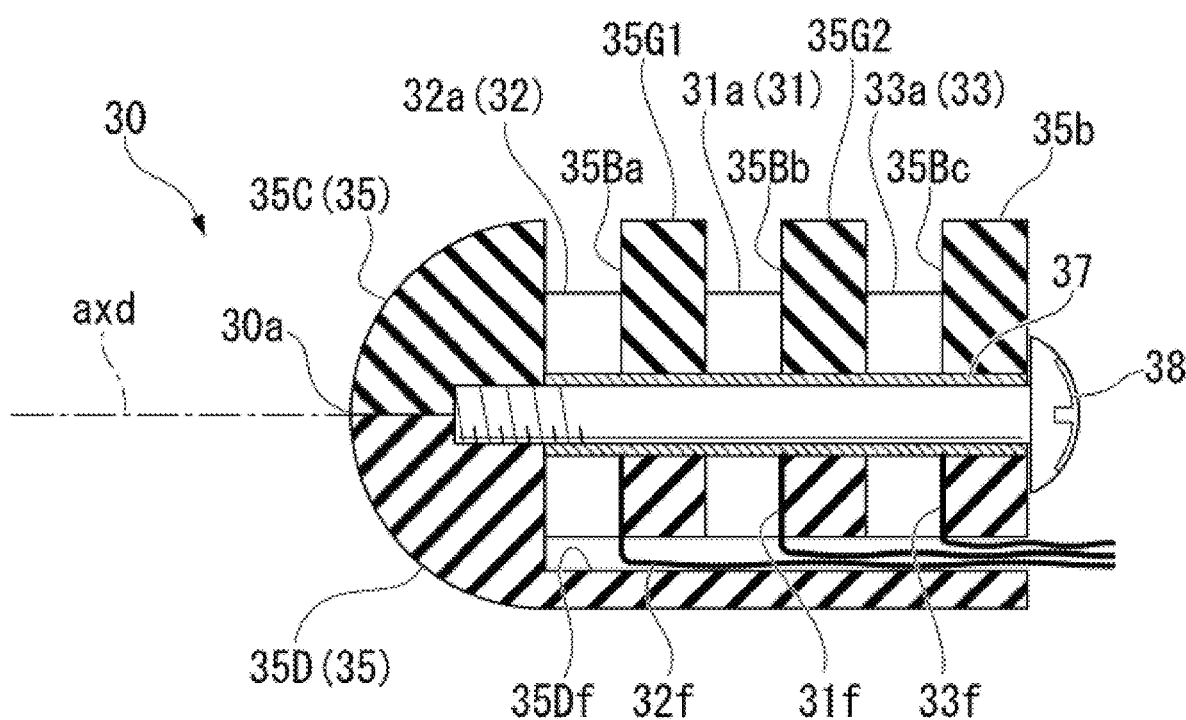
FIG. 18 shows a section along the axial direction in order to illustrate another example of the sensor relating to the fourth embodiment of the present invention.

FIG. 18 shows a section along the axial line direction in order to illustrate another example of the sensor relating to the present embodiment. In the sensor 30 relating to the present embodiment, the casing 35B is a single-piece member. As shown in FIG. 18, however, the casing 35B may include two separate members divided by a plane parallel to the axial line axd.

In the present example, an upper casing 35C has the window portions 35Ba to 35Bc, and a lower casing 35D has a line passage 35Df in communication with the outer peripheral surfaces 31a, 32a, 33a and extending in the direction along the axial line axd. The line passage 35Df is open at the base end portion 35b side and closed at the front end 30a side.

In the present example, the output lines are flexible substrates 31f, 32f, 33f.

The output line connected to the first electrode 31 is formed by the flexible substrate 31f and interposed between the first electrode 31 and the attracting portion 35. A portion of the flexible substrate 31f that is in contact with the first electrode 31 is electrically conductive as, for example, coating has been removed and thus in electrical communication with the first electrode 31. The electrodes 31 to 33, which are formed by magnets, are attracted to each other due to their magnetic force. Accordingly, the flexible substrate 31f is fixed while being sandwiched between the first electrode 31 and the attracting portion 35.

As a result, the flexible substrate 31f can be fixedly connected to the first electrode 31 without the use of an adhesive agent or the like and with electrical connection being maintained. In the same manner, in the sensor 30 relating to the present embodiment, the flexible substrate 32f is fixedly connected to the second electrode 32, and the flexible substrate 33f is fixedly connected to the third electrode 33. The flexible substrates 31f, 32f and 33f are connected to the sensing unit 5 via the internal space within the line passage 35Df.

The present example can produce the same effects as the above-described embodiments.

Figure 19:
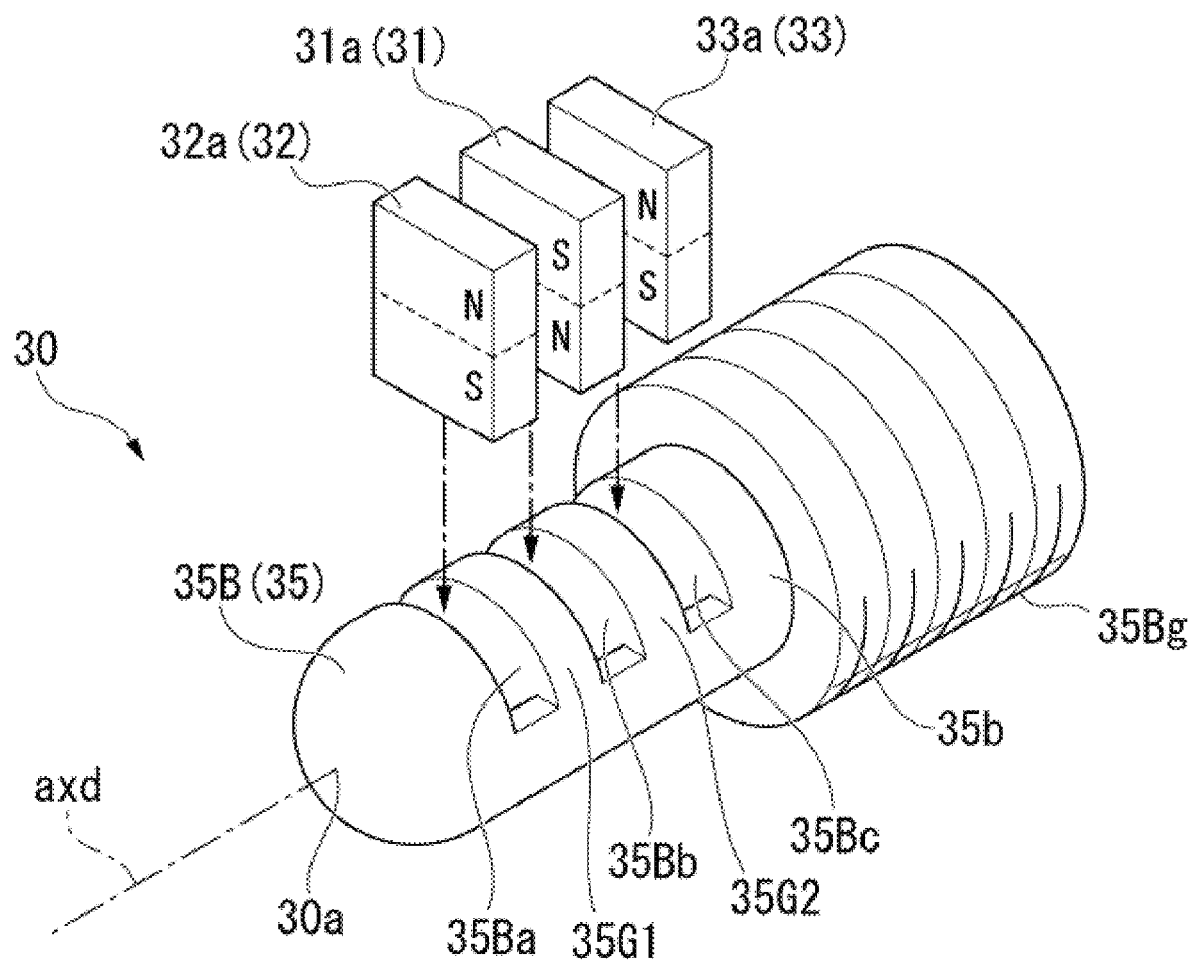
FIG. 19 is an exploded perspective view showing another example of a sensor relating to a fifth embodiment of the present invention.

The following describes a sensor relating to a fifth embodiment of the present invention with reference to the drawings. FIG. 19 is an exploded perspective view showing the sensor relating to the fifth embodiment. The fifth embodiment is different from the above-described fourth embodiment in terms of the shape of the magnets. The common constituents are assigned with the same reference numerals and are not described here.

In the sensor 30 relating to the present embodiment, the first, second and third electrodes 31, 32 and 33 have a substantially rectangular outline when seen in the direction along the axial line axd. The electrodes 31 to 33 are shaped like a rectangular flat plate. The first, second and third electrodes 31, 32 and 33 all have substantially the same shape.

In the sensor 30 relating to the present embodiment, the direction of magnetization in the electrodes 31 to 33 and the positioning of the electrodes 31 to 33 relative to the attracting portion 35, which is the casing 35B, are substantially the same as in the above-described third embodiment. Specifically, the first, second and third electrodes 31, 32 and 33 are rectangular plate members centered around the axial line axd. The first electrode 31, second electrode 32 and third electrode 33 are stacked in the axial line axd direction in the order of the second electrode 32, first electrode 31 and third electrode 33 from the front end 30a toward the base end along the axial line axd direction.

The second electrode 32, first electrode 31 and third electrode 33 are parallel to each other, arranged concentrically and next to each other in the direction along the axial line axd. The second electrode 32, first electrode 31 and third electrode 33 are arranged such that the four sides of their respective outer peripheral surfaces 31a to 33a form a flush surface of the same prism. The second electrode 32, first electrode 31 and third electrode 33 have the same radial size (the length of one of the sides of the rectangle, or the length of the diagonal of the rectangle) in the direction orthogonal to the axial line axd.

In all of the first, second and third electrodes 31, 32 and 33, which are magnets, the direction of magnetization extends in the radial direction of the sensor 30. The first electrode 31 has an outer peripheral surfaces 31a radially bounding the outer periphery and divided into four end surfaces. The first electrode 31 is magnetized such that each pair of end surfaces opposing with respect to the axial line axd includes different poles. The second and third electrodes 32 and 33 have an outer peripheral surface 32a, 33a divided into four end surfaces. The second and third electrodes 32 and 33 are also magnetized such that each pair of end surfaces opposing with respect to the axial line axd includes different poles.

The poles in the outer peripheral surface 31a of the first electrode 31 are opposite to the poles in the outer peripheral surfaces 32a and 33a of the second and third electrodes 32 and 33. In other words, the electrodes 31, 32, 33, which are adjacent to each other along the axial line axd, are magnetized such that different poles are adjacent. That is to say, the first electrode 31 is a magnet magnetized in the same manner as the second and third electrodes 32 and 33 but rotated around the axial line axd by 180°.

For example, as shown in FIG. 19, the first electrode 31 is magnetized such that the lower end surface of the outer peripheral surface 31a is the N pole. The second and third electrodes 32 and 33 are magnetized such that the upper end surface of their respective outer peripheral surfaces 32a and 33a is the N pole. The direction of magnetization can be reversed in all of the electrodes 31 to 33.

Arranged in the above-described manner, the electrodes 31 to 33, which are magnets, are attracted to each other in the axial line axd direction through their magnetic force. As a result, the electrodes 31 to 33 can be arranged to overlap each other in the axial line axd direction and secured onto the attracting portion 35 without the use of an adhesive portion such as an adhesive agent. Furthermore, since the electrodes 31 to 33 have a rectangular outline, the direction of magnetization can be easily fixed when the electrodes 31 to 33 are attached to the casing 35B.

In the present embodiment, the third electrode 33, the first electrode 31 and the second electrode 32, which are stacked on each other along the axial line axd, all similarly have a center hole through which a fastening member 38 (in the illustrated embodiment, a screw) is inserted and centered around the axial line axd.

This embodiment can also produce the same effects as the above-described embodiments.

Figure 20:
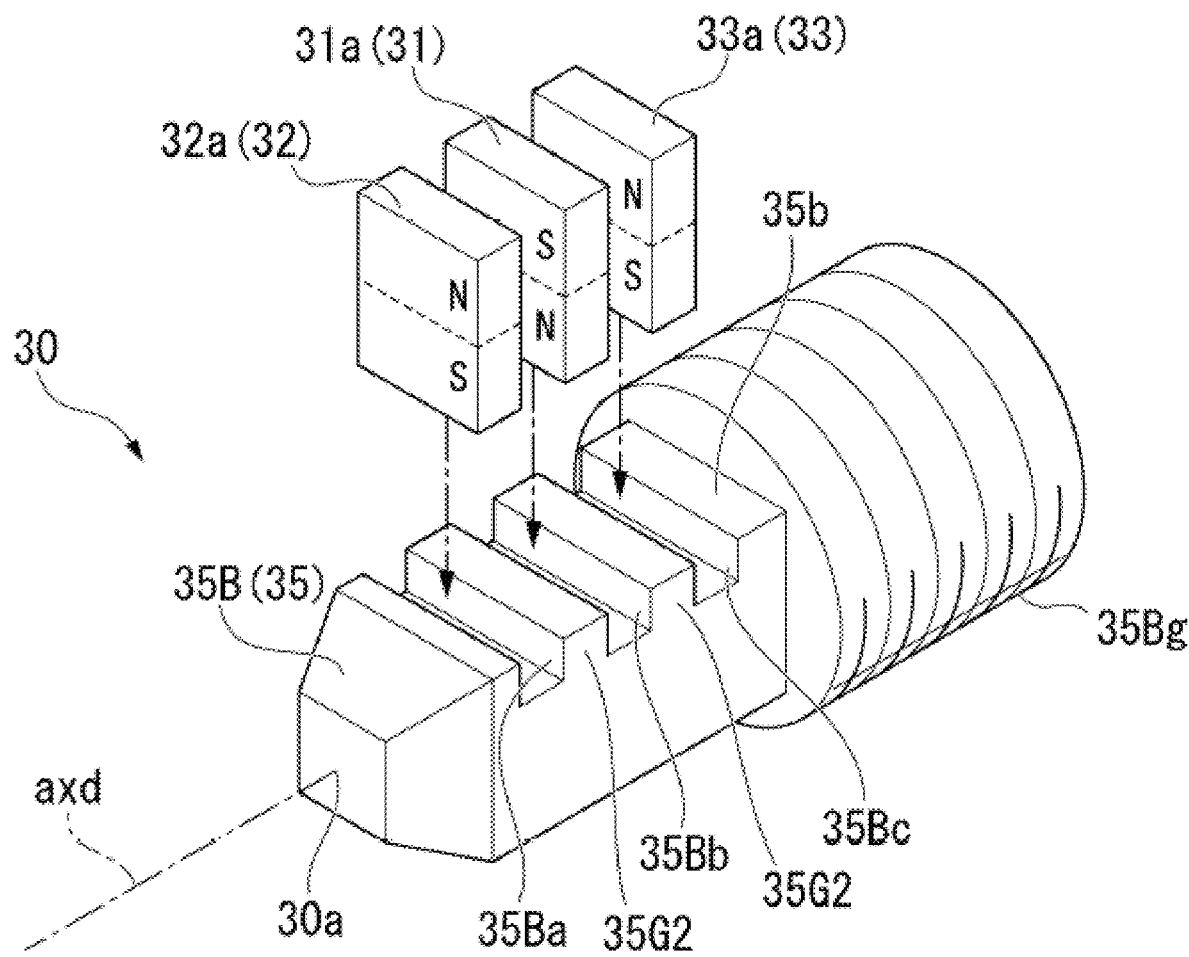
FIG. 20 is an exploded perspective view showing another example of the sensor relating to the fifth embodiment of the present invention.

FIG. 20 is an exploded perspective view showing another example of the sensor relating to the present embodiment. In the sensor 30 relating to the present embodiment, the casing 35B has a substantially cylindrical outer shape. As shown in FIG. 2, however, the casing 35B can alternatively have a substantially prismatic outer shape. In the present example, the electrodes 31 to 33 can be positioned relative to the casing 35B such that the sides of the electrodes 31 to 33, which have a rectangular outline, can be parallel to the sides of the casing 35B, which has a substantially prismatic shape. In this way, the direction of magnetization can be more easily fixed when the electrodes 31 to 33 are attached to the casing 35B.

The present example can also produce the same effects as the above-described embodiments.

Figure 21:
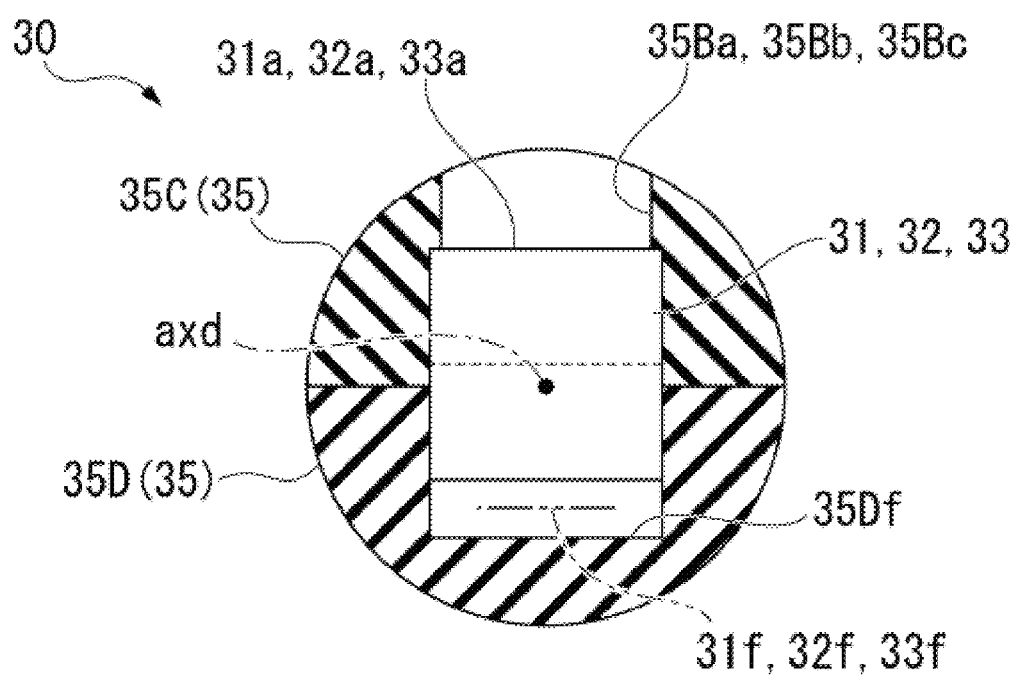
FIG. 21 shows a section orthogonal to the axial direction in order to illustrate another example of the sensor relating to the fifth embodiment of the present invention.

FIG. 21 is an exploded perspective view showing another example of the sensor relating to the present embodiment. In the preceding description of the sensor 30 relating to the present embodiment, the casing 35B is a single-piece member. As shown in FIG. 21, however, the casing 35B may include two separate members divided by a plane parallel to the axial line axd. In the present example, the electrodes 31 to 33, which are magnets, are shaped like a flat plate having a rectangular outline, the line passage 35Df is provided, and the output lines are the flexible substrates 31f, 32f, 33f.

In the present example, the upper casing 35C is provided with the window portions 35Ba to 35Bc. The window portions 35Ba to 35Bc have a slightly smaller circumferential size than the electrodes 31 to 33, as shown in FIG. 21. The line passage 35Df is formed in the lower casing 35D such that the line passage 35Df is in communication with the outer peripheral surfaces 31a, 32a, 33a and extends along the axial line axd. The line passage 35Df is open at the base end portion 35b side and closed at the front end 30a side.

In the present example, the output line connected to the first electrode 31 is also formed by the flexible substrate 31f, which is interposed between the first electrode 31 and the attracting portion 35. A portion of the flexible substrate 31f that is in contact with the first electrode 31 is electrically conductive as, for example, coating has been removed and thus in electrical communication with the first electrode 31. The electrodes 31 to 33, which are formed by magnets, are attracted to each other due to their magnetic force. Accordingly, the flexible substrate 31f is secured while being sandwiched between the first electrode 31 and the attracting portion 35.

As a result, the flexible substrate 31f can be fixedly connected to the first electrode 31 without the use of an adhesive agent or the like and with the electrical connection being maintained. In the same manner, in the sensor 30 relating to the present example, the flexible substrate 32f is fixedly connected to the second electrode 32, and the flexible substrate 33f is fixedly connected to the third electrode 33. The flexible substrates 31f, 32f and 33f are connected to the sensing unit 5 via the internal space within the line passage 35Df.

In the present example, the lower casing 35D can be assembled by inserting the electrodes 31 to 33 into the upper casing 35C and interposing the flexible substrates 31f, 32f and 33f, which have been inserted into the line passage 35Df. In this way, the assembling can be more easily completed.

The present example can also produce the same effects as the above-described embodiments.

Figure 22:
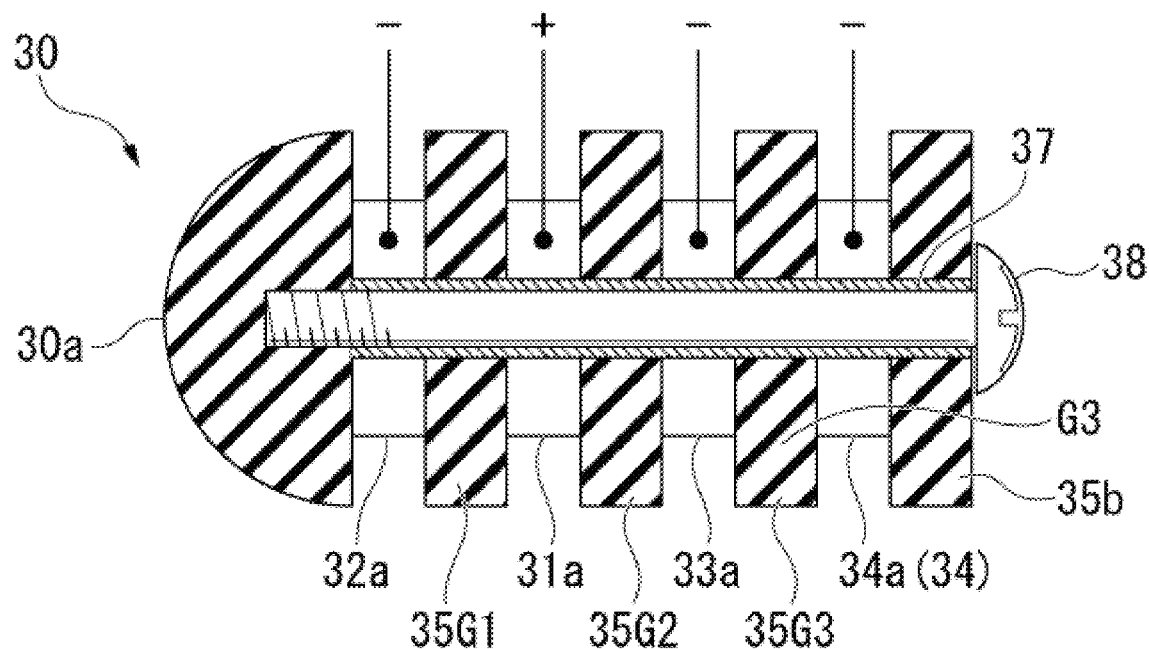
FIG. 22 is a sectional view taken along the axial direction and showing how the electrodes are arranged in a sensor relating to a sixth embodiment of the present invention.

The following describes a sixth embodiment of the sensor relating to the present invention with reference to the drawings. FIG. 22 is a sectional view taken along the axial line and showing how the electrodes are arranged in the sensor relating to the present embodiment. The sixth embodiment is different from the above-described third embodiment in terms of the number of the electrodes. The common constituents are assigned with the same reference numerals and are not described here.

The sensor 30 relating to the present embodiment has, in addition to the electrodes 31 to 33, an attracting protrusion 35G3 forming a gap G3 and a fourth electrode 34 between the third electrode and the base end portion 35b. The electrodes 31 to 34 are stacked on each other in the axial line axd direction in the order of the second electrode 32, the first electrode 31, the third electrode 33 and the fourth electrode 34 from the front end 30a toward the base end portion 35b along the axial line axd direction.

In the present embodiment, the shape of the fourth electrode 34 and the positioning of the fourth electrode 34 relative to the gap G3 and the attracting protrusion 35G3 are similar to the shape of the first electrode 31 and the positioning of the first electrode 31 relative to the attracting protrusions 35G1, 35G2 and the gaps G1, G2. In the present embodiment, the direction of magnetization in the fourth electrode 34 is the same as in the first electrode 31 and opposite to that in the adjacent third electrode 33.

In the sensor 30 relating to the present embodiment, the detecting units corresponding to the electrodes 31 to 34 constitute two parallel systems. As shown in FIG. 22, the detecting units can form two stages.

Specifically, the second electrode 32 near the front end 30a and the first electrode 31 positioned at the center in the axial line axd direction constitute a first-stage detecting unit. The second electrode 32 near the front end 30a and the third electrode 33 at the opposite position in the axial line axd direction constitute a parallel detecting unit. Furthermore, the first electrode 31 and the fourth electrode 34 constitute a second-stage detecting unit. In FIG. 22, the electrode pairs constituting the detecting units are denoted by assigning the sign "+" to the output line of the first electrode 31 and "−" to the output lines of the other electrodes 32 to 34.

In the present embodiment, the sensing unit 5 is configured to sense a change in electrical resistance between the first electrode 31 and the second electrode 32. If the conductive particles mp contained in the lubricating oil in the mechanism 1 are gathered in the vicinity of the attracting protrusion 15G1, this causes a drop in electrical resistance (or a short circuit) between the first electrode 31 and the second electrode 32 to which voltage is being applied, resulting in a change in output level of the output lines. The sensing unit 5 senses such a change in electrical resistance, thereby predicting a failure of the parts constituting the mechanism 1.

In the present embodiment, the sensing unit 5 is configured to sense a change in electrical resistance between the second electrode 32 and the third electrode 33. If the conductive particles mp contained in the lubricating oil in the mechanism 1 are gathered in the vicinity of the attracting protrusion 35G2, this causes a drop in electrical resistance (or a short circuit) between the first electrode 31 and the third electrode 33 to which voltage is being applied, resulting in a change in output level of the output lines. The sensing unit 5 senses such a change in electrical resistance, thereby predicting a failure of the parts constituting the mechanism 1.

In the present embodiment, the sensing unit 5 predicts a failure of the parts constituting the mechanism 1 also based on, for example, a change in electrical resistance caused by the gathering of the conductive particles mp in the vicinity of both of the attracting protrusions 35G1 and 35G3. If the conductive particles mp contained in the lubricating oil are gathered in the vicinity of both of the attracting protrusions 35G1 and 35G3, this causes a drop in electrical resistance (or a short circuit) between the second electrode 32 and the fourth electrode 34 to which voltage is being applied, resulting in a change in output level of the output lines. The sensing unit 5 senses such a change in electrical resistance, thereby predicting a failure of the parts constituting the mechanism 1. This sensing is not made possible until the conductive particles mp are gathered in the vicinity of both of the attracting protrusions 35G1 and 35G3.

As described above, the change in electrical resistance experienced by the detecting unit corresponding to the first electrode 31 is used to detect a change in electrical resistance in one attracting protrusion, which is the attracting protrusion 35G1. Likewise, the change in electrical resistance experienced by the detecting unit corresponding to the third electrode 33 is used to detect a change in electrical resistance in one attracting protrusion, which is the attracting protrusion 35G2. On the other hand, the change in electrical resistance experienced by the detecting unit corresponding to the fourth electrode 34 is used to detect a change in electrical resistance in two attracting protrusions, which are the attracting protrusions 35G1 and 35G3. This means that the plurality of detecting units are capable of sensing different conditions. In other words, the detecting units are configured to detect a change in electrical resistance in two stages. Accordingly, the reliability of the failure prediction can be improved.

For the second electrode 32, first electrode 31, third electrode 33 and fourth electrode 34, which are arranged next to each other in the axial line axd direction, FIG. 22 shows the detecting unit configuration "−" "+" "−" "−." It is, however, possible to provide for detecting unit configuration "−" "−" "+" "−." Furthermore, detecting unit configurations "+" "−" "−" "−" and "−" "−" "−" "+" are also realizable, in which case a change in electrical resistance can be detected in three stages.

This embodiment can also produce the same effects as the above-described embodiments.

Figure 23:
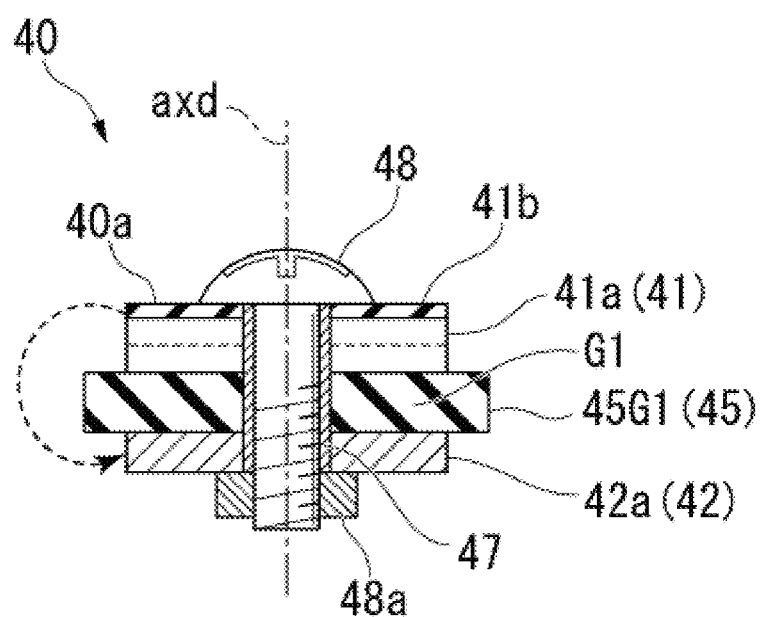
FIG. 23 is a sectional view taken along the axial direction and showing a sensor relating to a seventh embodiment of the present invention.
Figure 24:
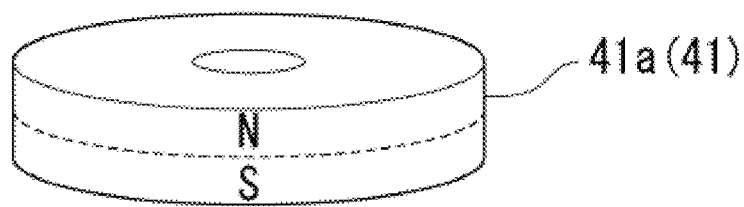
FIG. 24 shows magnets included in the sensor relating to the seventh embodiment of the present invention.

The following describes a sensor relating to a seventh embodiment of the present invention with reference to the drawings. FIG. 23 is a sectional view taken along the axial direction and showing the sensor relating to the seventh embodiment of the present invention. FIG. 24 is used to illustrate the magnets of the sensor relating to the present embodiment. In FIG. 23, the reference numeral 40 denotes the sensor. The seventh embodiment is different from the above-described third embodiment in terms of the configurations of the sensor. The constituents of the mechanism 1 illustrated in FIG. 1 are not described here.

As shown in FIG. 23, the sensor 40 relating to the present embodiment has a substantially cylindrical outer shape around an axial line axd. The sensor 40 includes a first electrode 41, a second electrode 42, a fastening member 48, and an attracting portion (catching portion) 45.

In the sensor 40, the first electrode 41, second electrode 42 and attracting portion 45 are plate members having a circular outline centered around the axial line axd when seen in the axial line axd direction. The first electrode 41, attracting portion 45 and second electrode 42 all have substantially the same outline and substantially the same thickness. The first electrode 41, attracting portion 45 and second electrode 42 are stacked on each other in the axial line axd direction in the order of the first electrode 41, attracting portion 45 and second electrode 42 from an upper end surface 40a along the axial line axd direction.

The first electrode 41, attracting portion 45 and second electrode 42 are arranged next to each other in the direction along the axial line axd and parallel to each other concentrically. The first and second electrodes 41, 42 are arranged such that their respective outer peripheral surfaces 41a, 42a form the same or flush cylindrical surface. An electrode plate 41b, which serves as, for example, a washer, is arranged on the first electrode 41 on the upper end surface 40a side.

The first and second electrodes 41 and 42 are spaced away from each other in the direction along the axial line axd. A gap G1 is formed between the first electrode 41 and the second electrode 42. The first electrode 41 is a magnet. The magnet is a permanent magnet. The first electrode 41 is magnetized in the direction along the axial line axd, as shown in FIG. 24. The second electrode 42 is made of an electrically conductive magnetic material such as, for example, iron, ferrite, or silicon steel.

The attracting portion 45 is shaped like a circular plate having a larger radial size than the first and second electrodes 41 and 42. The attracting portion 45 has an attracting protrusion 45G1 filling the gap G1 between the first electrode 41 and the second electrode 42 and protruding radially outward beyond the outer peripheral surfaces 41a, 42a. The thickness, in the axial line axd direction, of the gap G1 between the first electrode 41 and the second electrode 42 is larger than the size of the conductive substance that can be contained in the lubricating oil. For example, the conductive substance has a size of approximately 1.0 μm to 100 μm. The thickness of the gap G1 is preferably determined such that no short circuit is created by the iron powder resulting from initial wear period. In the case where the gap G1 is formed of a plurality of members, the members have the same size in the direction along the axial line axd.

The first electrode 41, attracting portion 45 and second electrode 42 all have therein a through hole, through which the fastening member 48 (in the illustrated embodiment, a bolt) is inserted. The fastening member 48 is inserted through the through holes, so that the first electrode 41, attracting portion 45 and second electrode 42 are secured to each other. The bolt (fastening member) 48 is fastened by a nut 48a. A tube 47 is provided radially outside the bolt (fastening member) 48 and surrounds the bolt 48. The tube 47 contributes to keep the first and second electrodes 41 and 42 and the bolt 48 insulated from each other and to secure the first and second electrodes 41 and 42 and the attracting protrusion 45G1 relative to each other at predetermined positions in the radial direction. The present embodiment can be practiced without the tube 47.

Between the second electrode 42 and the first electrode 41, which is a magnet, magnetic flux lines run radially outside the attracting protrusion 45G1 to connect the second and first electrodes 42 and 41 in the direction along the axial line axd, as shown in FIG. 23.

Output lines are connected to the first and second electrodes 41 and 42. The first and second electrodes 41 and 42 are respectively electrically connected to the sensing unit 5 (see FIG. 1) via the output lines. The first and second electrodes 41 and 42 are insulated from each other. The first electrode 41 and the second electrode 42 form a pair of electrodes, and the attracting portion 45 arranged between the paired electrodes constitutes a single detecting unit together with the pair of electrodes.

The sensing unit 5 is configured to sense a change in electrical resistance between the first electrode 41 and the second electrode 42. The sensing unit 5 includes a sensor drive circuit for predicting a failure of the parts constituting the mechanism 1 based on, for example, a change in electrical resistance caused in the axial line axd direction by the gathering of the conductive substance in the vicinity of the attracting portion 45. If the conductive substance contained in the lubricating oil is gathered in the vicinity of the attracting portion 45, this causes a drop in electrical resistance (or a short circuit) between the first electrode 41 and the second electrode 42 to which voltage is being applied, resulting in a change in output level of the output lines. The sensing unit 5 senses such a change in electrical resistance, thereby predicting a failure of the parts constituting the mechanism 1.

The drop in electrical resistance may be indicated by an ON signal and an OFF signal corresponding to electrical disconnection and connection. The sensing unit 5 may sense two states of electrical disconnection and connection (hereinafter, may be referred to as "perform digital sensing"). The sensing unit 5 may be connected to a higher-level control device (not shown) such as a manipulator in a wired or wireless manner. The higher-level control device may be configured to, upon reception of a signal from the sensing unit 5, issue an alert for demanding maintenance of, for example, the speed reducer 2 with a predetermined notifying device (for example, a display or voice output device).

According to the sensor 40 relating to the present embodiment, the gap G1 for detecting the conductive particles mp extends along the outer peripheral surfaces 41a and 42a and in the direction along the axial line axd. In this way, when compared with the case where such a gap for detecting conductive particles extends in the radial direction on the end surface of the sensor 40, the sensor 40 can be reduced in size without compromising the detection sensitivity. Since the magnet is exposed on the surface of the sensor and serves also as the first electrode 41 and the magnetic flux lines are formed radially outside the attracting portion 45, the conductive particles mp can be attracted highly efficiently. Thus, the size reduction can not result in lower attraction efficiency. The detection sensitivity can be determined by the size in the direction along the axial line axd. Accordingly, an increase in radial size can be prevented even if measures are taken to prevent initial abrasion powder from causing erroneous operation. Furthermore, the sensor 40 of the present embodiment can be constituted by a reduced number of parts, assembled easily and manufactured at a reduced cost.

Figure 25:
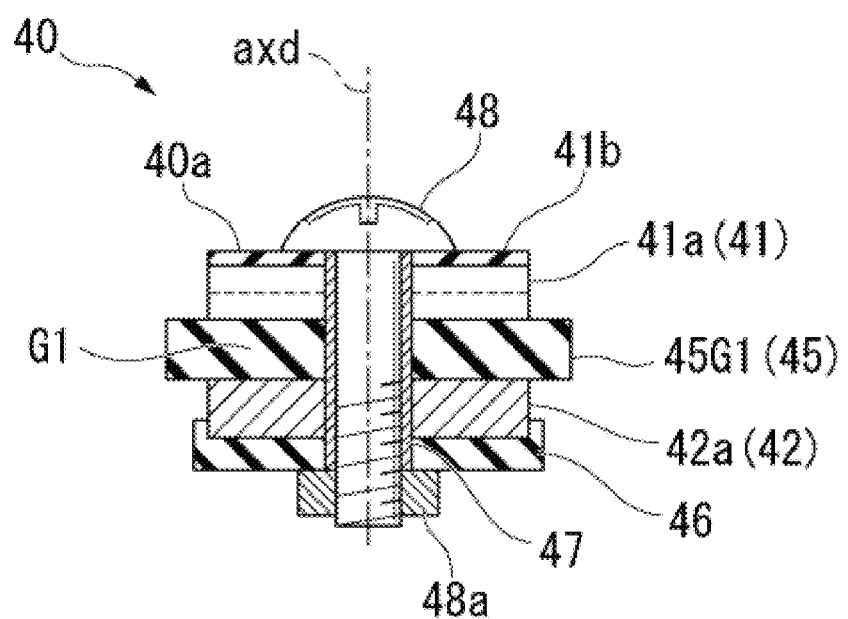
FIG. 25 is a sectional view taken along the axial direction and showing a sensor relating to an eighth embodiment of the present invention.
Figure 26:
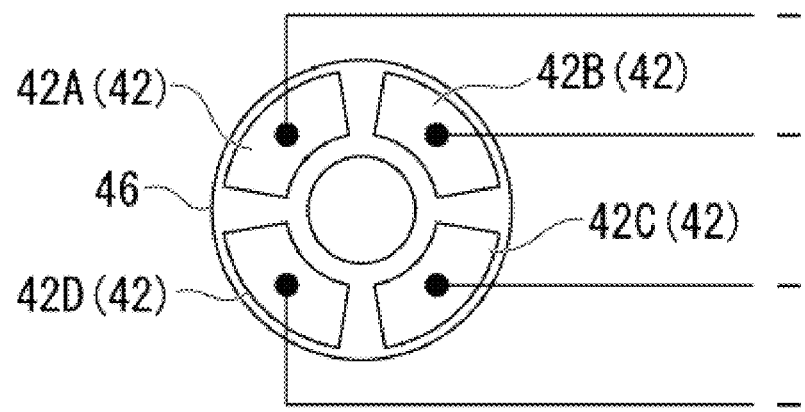
FIG. 26 shows how the electrodes are arranged in the sensor relating to the eighth embodiment of the present invention.

The following describes a sensor relating to an eighth embodiment of the present invention with reference to the drawings. FIG. 25 is a sectional view taken along the axial direction and showing the sensor relating to the eighth embodiment of the present invention. FIG. 26 shows how the electrodes are arranged in the sensor relating to the present embodiment. The eighth embodiment is different from the above-described seventh embodiment in terms of the configurations of the second electrode and casing. Except for these different features, the common constituents are assigned with the same reference numerals and are not described here.

The sensor 40 relating to the eighth embodiment is configured to sense the amount of the conductive substance contained in the lubricating oil, similarly to the sensor 40 relating to the seventh embodiment described above. As shown in FIG. 25, the sensor 40 has a substantially cylindrical outer shape and includes a plurality of detecting units and a sensing unit 5 configured to output a signal when the detecting units experience a change in electrical resistance.

More specifically, the sensor 40 includes a first electrode 41, a plurality of second electrodes 42, and an attracting portion 45 disposed between the first electrode 41 and the second electrodes 42. The second electrodes 42 are insulated from each other by a casing 46 and the like. The first electrode 41 and one of the second electrodes 42 form a pair of electrodes, and the attracting portion 45 arranged between the paired electrodes constitutes a single detecting unit together with the pair of electrodes.

The casing 46 receives therein the four second electrodes 42A, 42B, 42C and 42D, which are divided from each other in the circumferential direction, so that their positions can be fixed, and insulates the four second electrodes 42A, 42B, 42C, 42D from each other, as shown in FIG. 26. The casing 46 can be made of the same resin as the attracting portion 45.

In the embodiment illustrated, the sensor 40 includes the four second electrodes 42A, 42B, 42C, and 42D, which are divided from each other in the circumferential direction, so that four detecting units are formed. There are no particular limitations on the number of the second electrodes 42 and the number of the detecting units. The magnet serving as the first electrode 41 in the sensor 40 produces magnetic flux lines between the first electrode 41 and a paired one of the second electrodes 42A, 42B, 42C, 42D. Thus, the conductive substance contained in the lubricating oil is attracted to the attracting portion 45. The first electrode 41 and each one of the second electrodes 42A, 42B, 42C, 42D correspond to a detecting unit positioned on the side surface of the sensor body.

If the conductive substance is gathered in the vicinity of the attracting portion 45 in this manner, the detecting units experience a change in electrical resistance. While no conductive particles are attracted, the detecting units exhibit the same electrical resistance. The direction of the detection performed by each of the detecting units is determined by the gap G1 and extends along the axial line axd.

The first electrode 41 and the second electrodes 42A. 42B, 42C, 42D are respectively connected to output lines as shown in FIG. 26, and each detecting unit is electrically connected to the sensing unit 5 via a corresponding one of the output lines. In this embodiment, the detecting units are connected in parallel to each other, and voltage is applied between the first electrode 41 and each of the second electrodes 42A, 42B, 42C, 42D by the same voltage source. The sensing unit 5 outputs a signal when a designated number of the detecting units experience a change in electrical resistance. For example, the sensing unit 5 may be configured to output a signal to a higher-level control device such as a manipulator when two or more of the detecting units experience a drop in electrical resistance, or configured to output a signal when all of the detecting units experience a drop in electrical resistance.

As described above, the sensor 40 includes the plurality of detecting units, and the sensing unit 5 outputs a signal when a designated number of the detecting units experience a drop in electrical resistance. In this way, the sensing unit 5 can be configured to output no signal when just one of the detecting units experiences a change in electrical resistance caused by a large-diameter conductive piece. Furthermore, in the sensor 40, the sensing unit 5 can be configured to output a signal under a designated condition. Therefore, the single sensor 40 can be configured to output a signal in a timely and optimal manner for individual users, who have different requests for failure prediction timing.

While no conductive particles are attracted, the detecting units all exhibit the same electrical resistance. This can lower the voltage to be applied to the sensor 40. The detecting units are connected in parallel to each other. This can lower the voltage applied between the paired electrodes in each detecting unit.

This embodiment can also produce the same effects as the above-described embodiments.

Figure 27:
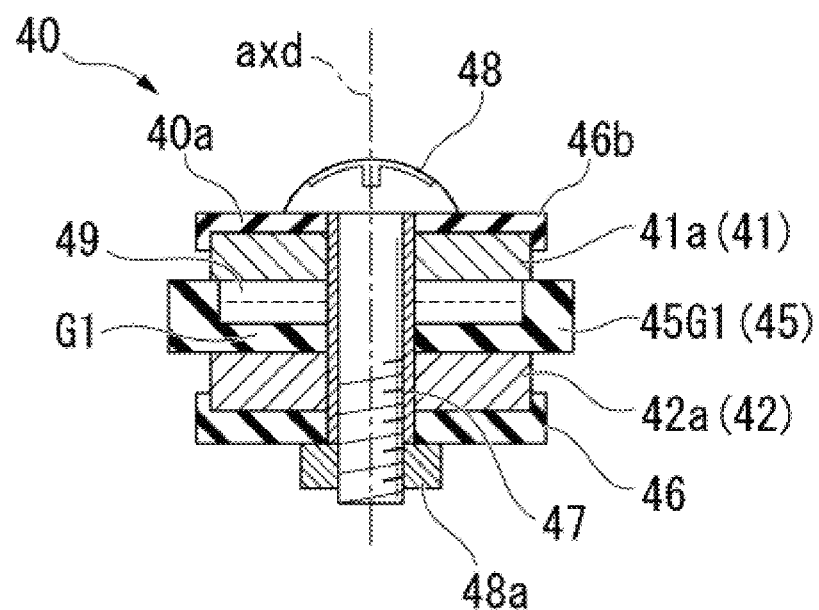
FIG. 27 shows a section along the axial direction in order to illustrate another example of a sensor relating to a ninth embodiment.

The following describes a sensor relating to a ninth embodiment of the present invention with reference to the drawings. FIG. 27 is a sectional view taken along the axial direction and showing the sensor relating to the ninth embodiment of the present invention. The ninth embodiment is different from the above-described seventh and eighth embodiments in terms of the attracting portion and magnet. Except for these different features, the common constituents are assigned with the same reference numerals and are not described here.

In the present embodiment, a magnet 49 is buried inside the attracting portion 45 and the outer peripheral surface of the magnet 49 is not externally exposed. The magnet 49 is in contact, in the direction along the axial line axd, with a surface of the first electrode 41 that faces the second electrode 42. Here, the first electrode 41 is a conductor shaped like a circular plate. The magnet 49 is preferably close to the first and second electrodes 41 and 42. The magnet 49 may be in contact with the second electrode 42. A casing 46*b* is arranged on the first electrode 41 on the upper end surface 40*a* side. The casing 46*b* covers a surface of the first electrode 41 that faces the upper end surface 40*a*.

The first electrode 41, magnet 49, attracting portion 45, second electrode 42 and casing 46 are stacked on each other in the direction along the axial line axd. The first and second electrodes 41 and 42 have substantially the same radial size, so that the outer peripheral surfaces 41*a* and 42*a* form a flush cylindrical surface. The magnet 49 has a smaller radial size than the first and second electrodes 41 and 42. The attracting portion 45 has an attracting protrusion 45G1 having a larger radial size than the first and second electrodes 41 and 42.

The attracting portion (insulator) 45 is, for example, made of an insulating non-magnetic material such as a resin. The magnet 49 produces magnetic flux lines between the first electrode 41 and the second electrode 42. Thus, the conductive substance contained in the lubricating oil is gathered to the vicinity of the attracting protrusion 45G1. Note that the term "detection region" denotes the region within which the lubricating oil circulates.

In the sensor 40 relating to the present embodiment, a sensing plane denotes the surface of the attracting protrusion 45G1 that protrudes radially outward beyond the cylinder connecting the outer peripheral surface 41*a* of the first electrode 41 and the outer peripheral surface 42*a* of the second electrode 42, which are substantially flush with each other. In other words, on the sensing plane, conductive abrasion powder is attracted between the first electrode 41 and the second electrode 42 by the magnetic flux lines, so that the first electrode 41 and the second electrode 42 are electrically connected. This causes a change in resistance between the first electrode 41 and the second electrode 42, which is to be detected. Note that the outer peripheral surface 41*a* of the first electrode 41 may not need to be flush with the outer peripheral surface 42*a* of the second electrode 42.

As the creepage distance between the first electrode 41 and the second electrode 42 increases, a larger amount of conductive abrasion powder can be attracted before the resistance between the first electrode 41 and the second electrode 42 drops to a threshold value or before a short circuit occurs. As the creepage distance between the first electrode 41 and the second electrode 42 decreases, a smaller amount of conductive abrasion powder can be attracted before the resistance between the first electrode 41 and the second electrode 42 drops to a threshold value or before a short circuit occurs.

The creepage distance between the first electrode 41 and the second electrode 42, which determines the detection sensitivity of the detecting units, depends on how much the attracting protrusion 45G1 of the attracting portion 45 protrudes. In other words, the creepage distance between the first electrode 41 and the second electrode 42, between which a short circuit may occur when conductive particles are gathered, can be changed by increasing or decreasing the protrusion height of the attracting protrusion 45G1 in the radial direction and the thickness of the attracting protrusion 45G1 in the direction along the axial line axd. The thickness of the attracting protrusion 45G1 in the direction along the axial line axd depends on the gap G1 and the thickness of the magnet 49.

The sensor 40 relating to the present embodiment has a group of attracting portions 45 that are different in protrusion height and thickness. The sensor 40 relating to the present embodiment can be assembled with a selected one of the attracting portions 45. In other words, the group of attracting portions 45 that are different from each other in thickness (the size in the axial line axd direction) and/or radial protrusion height serves as a sensitivity adjusting unit. In this way, the creepage distance between the first electrode 41 and the second electrode 42 can be selected from among a plurality of values by making a selection in the sensitivity adjusting unit. Having the sensitivity adjusting unit, the sensor 40 relating to the present embodiment is capable of setting the sensitivity at a predetermined level.

Speed reducers of different models (sizes) produce different amounts of iron powder (abrasion powder) during initial wear period. In the case of large speed reducers, a large amount of iron powder is produced by initial wear, and such iron powder may fill the electrical gap in the sensor between the electrodes 41 and 42. If such is the case, the sensor may react and erroneously operate. Therefore, the electrical gap in the sensor needs to be determined considering the model of the speed reducer, but this requirement may disadvantageously result in a larger sensor size in the diameter direction. To address this issue, the sensor 40 relating to the present embodiment has a sensitivity adjusting unit, which includes attracting portions 45 with different sizes. This configuration produces the same effects as the enlargement of the sensor in the diameter direction and thus allows the sensor 40 to maintain the size.

This embodiment can also produce the same effects as the above-described embodiments.

Modified Example 1

Furthermore, the sensor according to a modified example 1 relating to the above-described embodiment of the present invention may include the following configurations.

The sensor according to the modified example 1 includes:
a first electrode;
a second electrode spaced away from the first electrode with a gap being provided therebetween in an axial direction; and
an attracting portion arranged in the gap, the attracting portion having an outer peripheral surface made of an insulating material,
wherein the first electrode, the attracting portion and the second electrode are stacked on each other in the axial direction,
wherein conductive particles are attracted to the outer peripheral surface of the attracting portion, so that a short circuit is caused in the axial direction between the first electrode and the second electrode, resulting in a change in electrical resistance between the first electrode and the second electrode.
wherein a magnet is positioned closer in the axial direction to the first electrode at least than to the second electrode, and
wherein the magnet is arranged to form a magnetic flux line extending in the axial direction.

In the sensor according to the modified example 1, the first electrode is a magnet.

Modified Example 2

Furthermore, the sensor according to a modified example 2 relating to the above-described embodiment of the present invention may include the following configurations.

The sensor according to the modified example 2 includes:
a cylindrical sensor body,
wherein the sensor body includes:
a first electrode, an attracting portion, and a second electrode stacked on each other in an axial direction; and
a magnet magnetized in the axial direction, and
wherein conductive particles are attracted to an outer peripheral surface of the attracting portion, so that a short circuit is caused in the axial direction between the first electrode and the outer peripheral surface of the second electrode, resulting in a change in electrical resistance between the first electrode and the second electrode.

In the sensor according to the modified example 2, the second electrode is divided into portions in a circumferential direction of the sensor body.

What is claimed is:

1. A sensor comprising:
a first electrode made of a magnet;
a second electrode made of a magnet and arranged relative to the first electrode with a first gap being provided therebetween in a circumferential direction around an axial line of the sensor; and
a first attracting portion arranged in the first gap, the first attracting portion having an outer peripheral surface made of an insulating material,
wherein the first electrode, the first attracting portion, and the second electrode are arranged in this order in the circumferential direction,
wherein the first electrode and the second electrode are magnetized in a radial direction orthogonal to the axial line, and magnetization directions of the first electrode and the second electrode adjacent in the circumferential direction are opposite to each other in the radial direction,
wherein electric connection is established along the outer peripheral surface via conductive particles gathering to the first attracting portion, and
wherein the conductive particles are attracted to the outer peripheral surface of the first attracting portion, so that a short circuit is caused in the circumferential direction between the first electrode and the second electrode, resulting in a change in electrical resistance between the first electrode and the second electrode.

2. The sensor of claim 1, comprising:
a third electrode made of a magnet and spaced away from the first electrode with a second gap being provided therebetween in the circumferential direction, the third electrode being on a side of the first electrode opposite to the second electrode; and
a second attracting portion arranged in the second gap, the second attracting portion having an outer peripheral surface made of an insulating material,
wherein conductive particles are attracted to the outer peripheral surface of the second attracting portion, so that a short circuit is caused in the circumferential direction between the first electrode and the third electrode, resulting in a change in electrical resistance between the first electrode and the third electrode.

3. The sensor of claim 2, comprising:
a fourth electrode made of a magnet, spaced away from the second electrode with a third gap being provided therebetween in the circumferential direction, and spaced away from the third electrode with a fourth gap being provided therebetween in the circumferential direction;
a third attracting portion arranged in the third gap, the third attracting portion having an outer peripheral surface made of an insulating material; and
a fourth attracting portion arranged in the fourth gap, the fourth attracting portion having an outer peripheral surface made of an insulating material,
wherein conductive particles are attracted to the outer peripheral surface of the third attracting portion, so that a short circuit is caused in the circumferential direction between the second electrode and the fourth electrode, resulting in a change in electrical resistance between the second electrode and the fourth electrode, and
wherein conductive particles are attracted to the outer peripheral surface of the fourth attracting portion, so that a short circuit is caused in the circumferential direction between the third electrode and the fourth electrode, resulting in a change in electrical resistance between the third electrode and the fourth electrode.

4. The sensor of claim 1, wherein outer peripheral surfaces of the first and second electrodes form a side surface of a columnar body.

5. The sensor of claim 1, wherein the first and second electrodes are arranged such that magnetic flux lines extend radially outward from outer peripheral surfaces of the first and second electrodes.

6. The sensor of claim 1, comprising:
a third electrode made of a magnet and spaced away from the first electrode with a second gap being provided therebetween in the circumferential direction, the third electrode being on a side of the first electrode opposite to the second electrode;
a fourth electrode made of a magnet, spaced away from the second electrode with a third gap being provided therebetween in the circumferential direction, and spaced away from the third electrode with a fourth gap being provided therebetween in the circumferential direction;

a second attracting portion arranged in the second gap, the second attracting portion having an outer peripheral surface made of an insulating material;

a third attracting portion arranged in the third gap, the third attracting portion having an outer peripheral surface made of an insulating material; and a fourth attracting portion arranged in the fourth gap, the fourth attracting portion having an outer peripheral surface made of an insulating material, wherein the first to fourth electrodes are disposed in four areas obtained by dividing the sensor into four in the circumferential direction, wherein the sensor is formed in a cylindrical shape, wherein the first to fourth attracting portions protrude radially outward beyond outer peripheral surfaces of the first to fourth electrodes, wherein the first to fourth electrodes are magnetized in the radial direction, and magnetization directions of circumferentially adjacent ones of the first to fourth electrodes are opposite to each other in the radial direction.

* * * * *